(12) United States Patent
Applebaum et al.

(10) Patent No.: US 8,677,934 B2
(45) Date of Patent: Mar. 25, 2014

(54) SEX-PEPTIDES RESISTANT TO PROTEOLYTIC DEGRADATION AND THEIR USE IN BIOLOGICAL CONTROL OF INSECTS

(75) Inventors: Shalom Applebaum, Rehovot (IL); Yael Heifetz, Rehovot (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 754 days.

(21) Appl. No.: 12/671,620

(22) PCT Filed: Jul. 30, 2008

(86) PCT No.: PCT/IL2008/001047
§ 371 (c)(1),
(2), (4) Date: Feb. 1, 2010

(87) PCT Pub. No.: WO2009/016627
PCT Pub. Date: Feb. 5, 2009

(65) Prior Publication Data
US 2011/0283945 A1    Nov. 24, 2011

Related U.S. Application Data

(60) Provisional application No. 60/952,785, filed on Jul. 30, 2007.

(51) Int. Cl.
*A01K 67/033* (2006.01)

(52) U.S. Cl.
USPC ..... 119/6.6; 435/69.1; 435/320.1; 435/252.2; 435/325; 435/6.11; 514/4.5; 536/23.1; 530/350

(58) Field of Classification Search
USPC ............. 119/6.5, 6.6; 435/69.1, 252.2, 320.1, 435/6.11, 6.12, 325, 252.3; 514/4.5; 536/23.1; 530/350
See application file for complete search history.

(56) References Cited

U.S. PATENT DOCUMENTS 6,380,159 B1    4/2002  Wolfner et al.
6,955,897 B2    10/2005 Wolfner et al.

OTHER PUBLICATIONS

Pilpel, N., Nezer, I., Applebaum, S.W., Heifetz, Y.,. Mating increases trypsin in female *Drosophila hemolymph*. Insect Biochem. Mol. Biol. 38, 320-330 (2008).
Brand, A.H., Perrimon, N., Targeted gene expression as a means of altering cell fates and generating dominant phenotypes. Development. 118, 401-415 (1993).
Wolfner, M.F., Heifetz, Y., Applebaum, S.W., Gonadal glands and their gene products. In: Comprehensive Molecular Insect Science (L.I. Gilbert, ed. in-chief; K. Iatrou and S.S. Gill, eds.) vol. 1: Reproduction and Development, Chapter 5, pp. 179-212 (2005).
Moshitzky, P., Gilbert, L.I., Applebaum S.W. Biosynthetic maturation of the corpus allatum of the female adult medfly, *Ceratitis capitata*, and its putative control. J. Insect Physiol. 49, 603-609 (2003).
Styger, D.. Molekulare Analyse des Sex peptidgens aus *Drosophila melanogaster*. Dissertation., Universität Zürich, Zürich. (1992).

(Continued)

*Primary Examiner* — T. Nguyen
(74) *Attorney, Agent, or Firm* — Browdy and Neimark, PLLC

(57) ABSTRACT

An isolated nucleic acid molecule comprising, or consisting of, a polynucleotide sequence encoding an oligopeptide capable of inducing post-mating depression of receptivity to mating in female insects, wherein said oligopeptide is resistant to proteolytic degradation, is provided for expression in sterile transgenic male insects useful in the control of insect populations.

16 Claims, 15 Drawing Sheets

(56) References Cited

OTHER PUBLICATIONS

Fan, Y., Rafaeli, A., Moshitzky, P., Kubli, E., Choffat, Y., Applebaum, S.W.. Common functional elements of *Drosophila melanogaster* seminal peptides involved in reproduction of *Drosophila melanogaster* and *Helicoverpa armigera* females. Insect Biochem. Mol. Biol. 30, 805-812 (2000).

Schmidt, T., Choffat, Y., Klauser, S., Kubli, E., . The *Drosophila melanogaster* sex-peptide: a molecular analysis of structure-function relationships. J Insect Physiol 39, 361-368 (1993).

Peng, J., Chen, S., Busser, S., Liu, H., Honegger, T., Kubli, E., . Gradual release of sperm bound sex-Peptide controls female postmating behavior in *Drosophila*. Curr Biol. 15, 207-213 (2005).

Kubli, E.,. Sex-peptides: seminal peptides of the *Drosophila* male. Cell Mol Life Sci. 60, 1689-1704 (2003).

Liu, H., Kubli, E.,. Sex-peptide is the molecular basis of the sperm effect in *Drosophila melanogaster*. Proc Natl Acad Sci U S A. 100, 9929-9933 (2003).

Fan, Y., Rafaeli, A., Gileadi, C., Kubli, E., Applebaum, S.W. . *Drosophila melanogaster* sex peptide stimulates juvenile hormone synthesis and depresses sex pheromone production in *Helicoverpa armigera*. J. Insect Physiol. 45, 127-133 (1999).

Cirera, S., Aguade, M., Evolutionary history of the sex-peptide (acp70A) gene region in *Drosophila melanogaster*. Genetics society of America 147, 189-197 (1997).

Cirera, S., Aguade, M., The sex-peptide gene (acp70A) is duplicated *Drosophila subobscura*. Gene 210, 247-254 (1998).

Davis, S.J., Chapman, T., Identification of genes expressed in the accessory glands of male Mediterranean fruit files (*Ceratitis capitata*). Insect Biochemistry and Molecular Biology 36, 846-856 (2006).

Chen, P.S., Stumm-Zollinger., Aigaki, T., Balmer, J., Blenz, M., Bohien, p., A male accessory gland paptide that regulates reproductive behavior of female *D. melanogaster*. Cell, vol. 54 291-298 (1998).

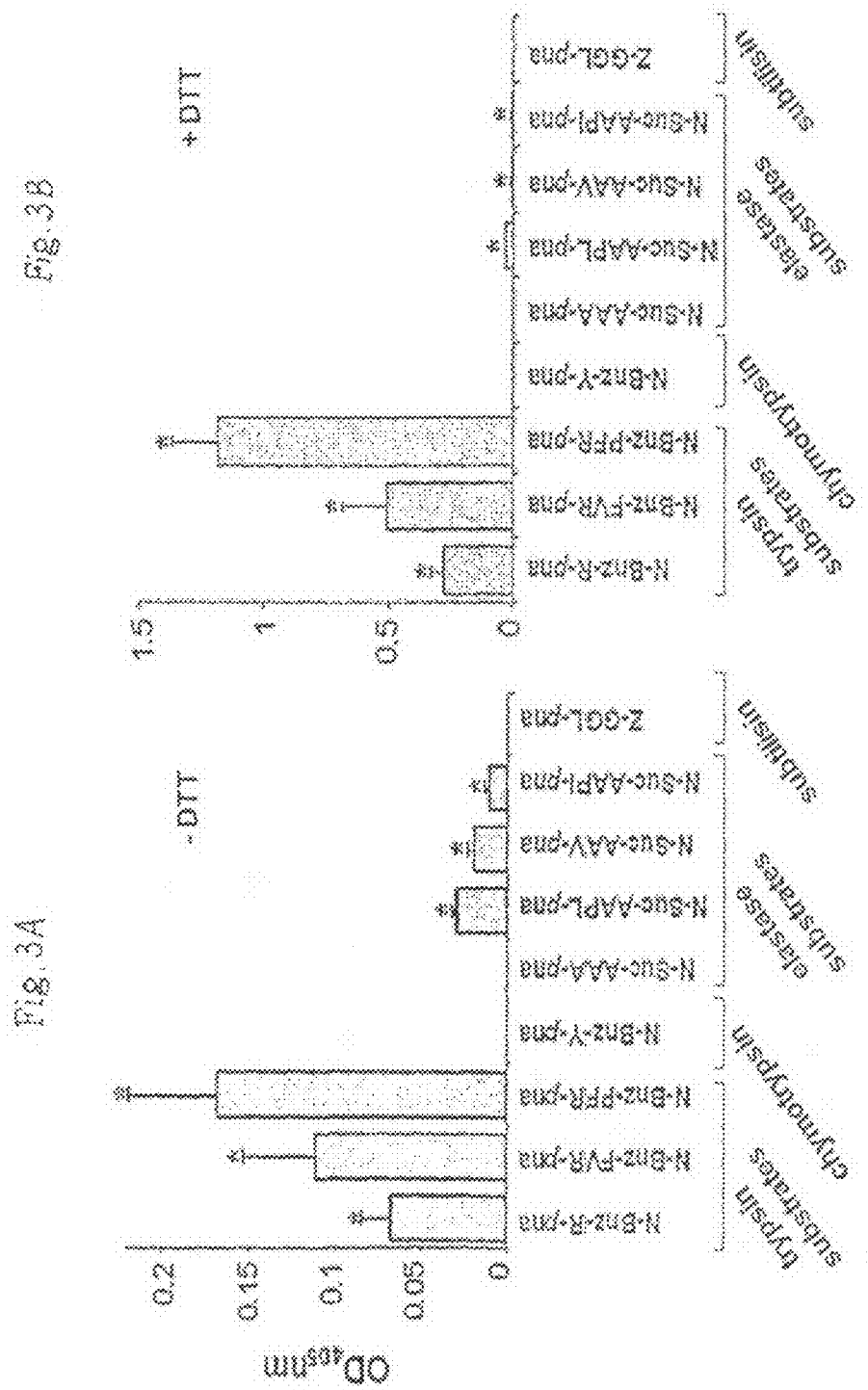

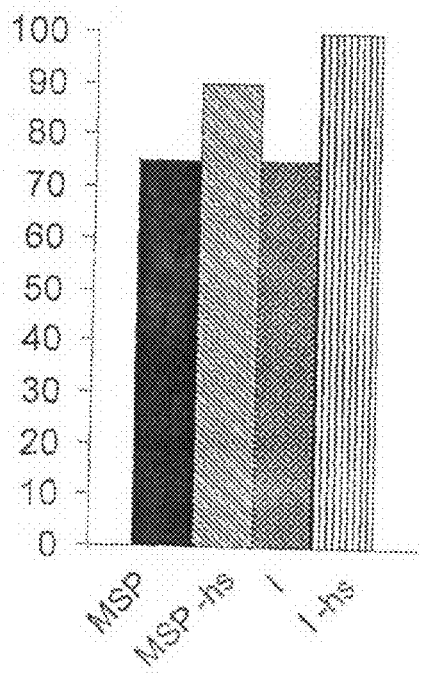 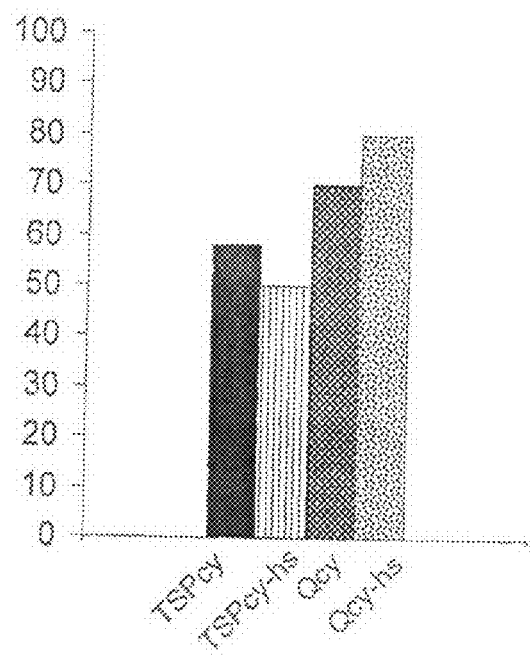

* Flies that do not express the
transgene, 24 hours post-heat-shock

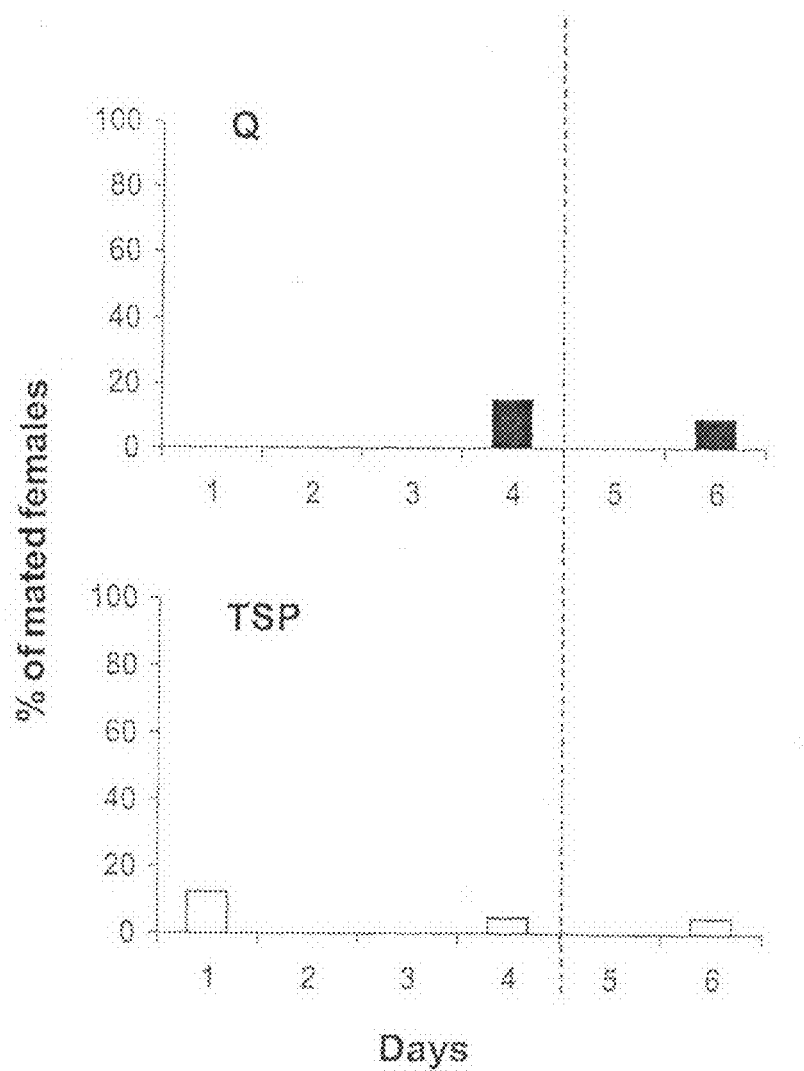

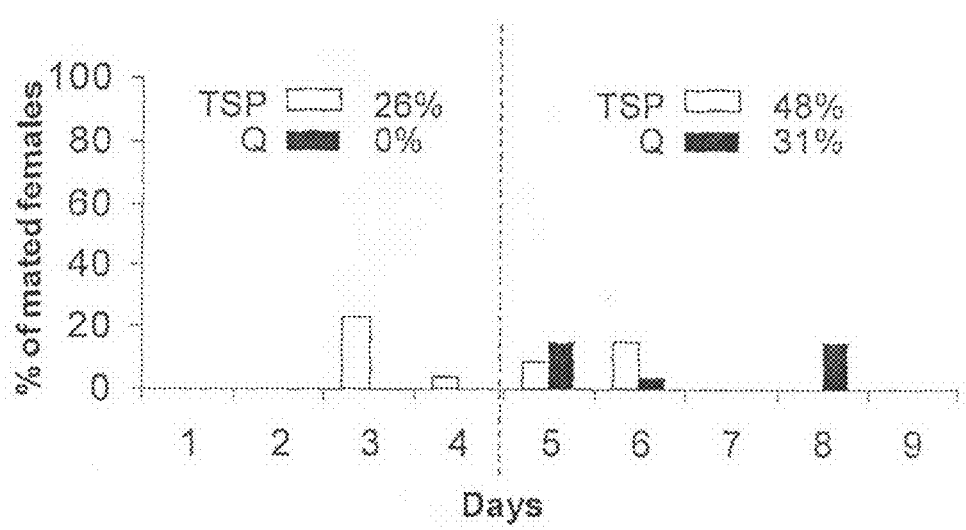

SEX-PEPTIDES RESISTANT TO PROTEOLYTIC DEGRADATION AND THEIR USE IN BIOLOGICAL CONTROL OF INSECTS

FIELD OF THE INVENTION

The present invention relates to methods of biological control of insect populations, and in particular to methods in which female wild-type insects, following mating with sterile transgenic males introduced into the insect population, become non-receptive to males for extended periods of time, thus being incapable of producing offspring.

BACKGROUND OF THE INVENTION

The Mediterranean fruit fly (Medfly, *Ceratitis capitata*), is possibly the most important agricultural pest of fruits and vegetables in temperate and subtropical regions. Being a qualitative pest, its status is not based on fruit biomass damaged, but rather on presence or absence of eggs or larvae.

The Sterile Insect Technique (SIT) is the accepted alternative for selective regional control of *C. capitata*. Examples of other insects that are successfully controlled using SIT or which are the targets for the development of such methods are Screwworm fly, Anopheles mosquito, Tsetse fly (*Glossina* spp), Painted Apple Moth (Lep: Lymantriidae) and Aedes mosquitoes.

Briefly, SIT is based on mass-production and release of irradiated sterile males, intended to compete numerically and qualitatively with feral fertile males by preventing the deposition of fertile eggs. SIT has been applied successfully to eradicate or reduce pest populations below a critical threshold of economic damage. The current protocol for *C. capitata* control is to release irradiated sterile males twice-weekly, throughout the year, in order to preclude subsequent possible mating with wild-type fertile males and prevent deposition of fertile eggs. There are several problems associated with the current practice: Firstly, irradiated males are less viable in the field and do not survive for as long as do feral males. Secondly, many of these facility-reared irradiated males mate for shorter periods and transfer less sperm to the female, and in consequence, such females subsequently re-mate sooner than those that have previously mated with feral males. Thirdly, under normal circumstances, unmated females, or females that have mated with irradiated (sterile) males, produce infertile eggs at a reduced rate, but their deposition in fruit is not in accord with the quarantine regulations of zero tolerance of infestation demanded.

WO 01/039599 discloses a new approach to SIT in which male insects homozygous for a dominant lethal gene are released and mate with wild insects thus producing progeny that are heterozygous for this dominant lethal gene and therefore invariably die.

Male-derived accessory gland proteins (Acps) are transferred to the female reproductive tract during mating and affect a variety of functions in the virgin female recipient involved in female reproductive maturation, behavior and fitness (reviewed in e.g. Wolfner, 2007). Most of the basic and physiological studies of the involvements of Acps in the post-mated female have been performed On the fruitfiy, *Drosophila melanogaster*. Several Acps have been disclosed in e.g. U.S. Pat. Nos. 6,955,897 6,380,159, one of which is an accessory gland protein which is toxic to insect cells and can be used to kill or inhibit the development of insects. The first and most thoroughly studied of the Acps to date is the *D. melanogaster* Sex Peptide (Acp70A, DrmSP) (see review by Wolfner et al., 2005). The gene encoding DrmSP has been cloned and sequenced (Styger, 1992). It is a single copy gene containing one intron, coding for a 55 amino acid peptide (FIG. 1). Secretion from the main cells of the accessory glands involves its release from the N-terminal signal peptide of 19 amino acids. Mature DrmSP is a linear, unblocked peptide of 36 amino acids, which contains two cysteines forming an S-S bridge. It bears several bioactive domains: a C-terminus regulating female post-mating non-receptivity (Schmidt et al., 1993), an N-terminus priming the functional maturation of the female corpus allatum (CA), resulting in up-regulation of the production of the major female gonadotropin—Juvenile Hormone (JH) (Moshitzlcy et al., 1996) and initiating a cascade of vitellogenesis, oogenesis and egg deposition in the mated female (Soller et al., 1997). Between these two termini, an internal sequence is proposed to up-regulate the humoral innate immunity of the post-mated female (Domanitskaya et al., 2007).

Soon after transfer of the seminal fluid to the female reproductive system, some Acps, including DrmSP, subsequently enter the female hemolymph (Pilpel et al., 2008). Initial activity of that part of the DrmSP molecule that is initially transferred intact into the female hemolymph presumably induces the combined physiological and behavioral responses of the mated female, which are significant but of short duration. Most of the DrmSP molecules bind to sperm via their N-termini and are stored in the female storage organs. From there, they are slowly released over time as truncated DrmSP lacking the N-terminus (hereafter T-SP) and are subsequently transferred to the hemolymph as such, thereby prolonging female post-mating non-receptivity. Allatal maturation and egg development are regulated maximally at this time by allatotrophins and allatostatins. The slow-release from stored sperm is the basis of the extended period of non-receptivity, termed the "sperm effect" (Peng et al., 2005).

SUMMARY OF THE INVENTION

The present invention relates, in one aspect, to an isolated nucleic acid molecule comprising, or consisting of, a polynucleotide sequence encoding an oligopeptide capable of inducing post-mating depression of receptivity to mating in female insects, wherein said oligopeptide is resistant to proteolytic degradation.

In one embodiment, the oligopeptide is made resistant to proteolytic degradation by trypsin due to the abolition of at least one trypsin cleavage site present in the wild type oligopeptide by conservative substitution of at least one arginine residue and/or at least one lysine residue, preferably substitution of an arginine or lysine residue with a glutamine residue.

In one preferred embodiment, said oligopeptide is derived from the *Drosophila melanogaster* sex peptide ("DrmSP") of the amino acid sequence as set forth in SEQ ID NO: 1, or from an active fragment of said peptide, said oligopeptide being modified such as not being degraded by proteolytic enzymes.

In another preferred embodiment, the oligopeptide is made resistant to proteolytic degradation by trypsin due to the abolition of at least one trypsin cleavage site present in the wild-type oligopeptide of SEQ ID NO: 1 by conservative substitution of at least one arginine residue and/or at least one lysine residue, preferably with a glutamine residue.

In another aspect, the present invention provides expression vectors comprising the nucleic acid molecules described above.

In a further aspect, the invention relates to transgenic insects comprising the nucleic acid molecules or expression vectors of the invention and expressing the modified sex peptide. In a preferred embodiment, the transgenic insect is a member of the Diptera order and most preferably it is an irradiated sexually sterile mature male adult *Ceratitis capitata*.

In another aspect, the present invention provides a method for controlling a population of insects in a natural environment comprising releasing the male transgenic insects into the environment at loci for population control.

BRIEF DESCRIPTION OF THE FIGURES

FIGS. 3A-B show that mated female hemolymph exhibits tryptic activity on synthetic chromogenic substrates. In order to conform to the single letter amino acid code, the substrate notation here differs from that in common use (e.g., N-Benzoyl-DL-Arg-p-Nitroanilide, abbreviated herein as N-Bnz-R-pna is commonly termed "BAPNA"). Activity assays were carried out in the absence (3A) or in the presence of dithiothreitol (DTT) (3B). All data represent background-subtracted values (see materials and methods). An absolute value corresponds to the net chromogenic response due to enzyme activity on the substrate. Error bars are means f standard error of means (SEM). Asterisks indicate statistical significance of cleavage of the different trypsin and elastase substrates ($p<0.05$). Hemolymph extracted from 250 mated *Drosophila* females, 4-day-old, were used for each assay; all assays were repeated 3 times in triplicates.

FIGS. 7A and 7C present the percentage of unmated transgenic females of two different lines, which carry the transgene but cannot express it, that mated once they were exposed to one male (black) or to two males (white); FIGS. 7B and 7D show the percent of female in the two lines that re-mated. In both lines a threshold (dashed line) could be drawn between 4-5 days. This threshold represent the time in which at least 50% of the wild-type females re-mated. n=20 for each treatment; m, mated; um, unmated.

FIGS. 8A-B show percentage of transgenic females that had not mated at 6 hrs post-heat-shock. Two lines, MSP and 1, that carry the transgenes but can not express the modified $DrmSP_{TSP}$ (8A) and two lines of cy females that are the progeny of hsp70-GAL4;UAS-$DrmSP_{TSP}$ females but are not carrying or expressing the transgenes (8B) were examined. n=40 females from each line.

FIG. 9B depicts a control experiment that confirms the absence of T-SP transcript in females that do not express T-SP (cy); DrmSP, *D. melanogaster* Sex Peptide.

FIG. 11 shows that the modified T-$SP_Q$ and wild-type T-SP induced female non-receptivity for 8 days post-mating also in the other independent lines examined. For all the transgenic lines, n=20. The dashed line represent the time that at least 50% of the females re-mated in the wild-type strain (4-5 days).

FIG. 14 shows that T-$SP_Q$ expressed in the male accessory glands and transmitted to the female in the male seminal fluid during mating prolongs female non-receptivity. Fraction of mated females as a function of time post-mating. The dashed line represent the time that at least 50% of the wild-type females re-mated (4-5 days). Black bars, T-SP; grey bars, T-$SP_Q$.

DETAILED DESCRIPTION OF THE INVENTION

Figure 1A:
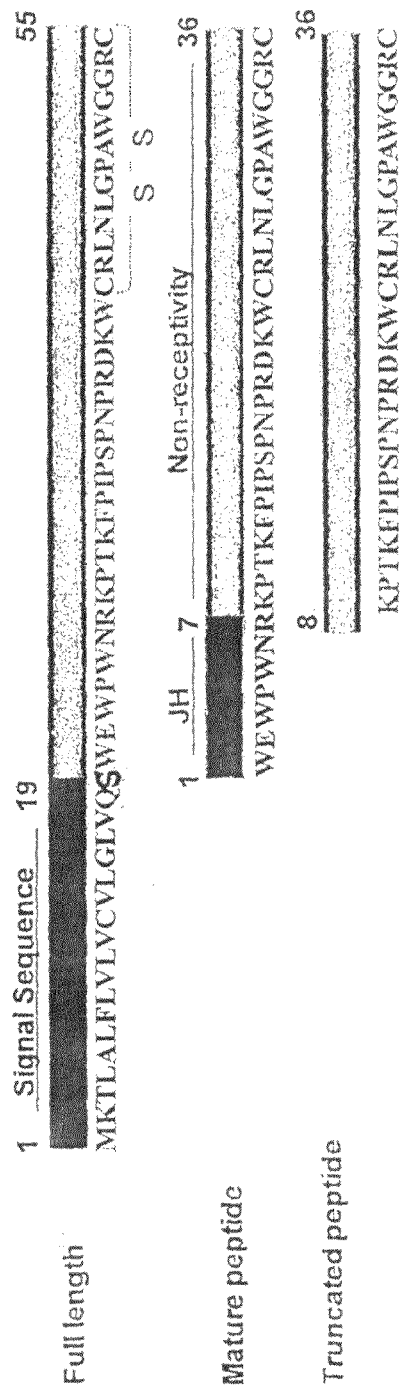
FIGS. 1A-B depict the DrmSP amino acid sequence and trypsin and chymotrypsin cleavage sites. (1A) Amino acid sequence of the precursor (SEQ ID NO: 1), mature (SEQ ID NO: 2) and truncated peptide (SEQ ID NO: 3). The 55 amino acid DrmSP precursor contains a 19 amino acid signal peptide (SEQ ID NO: 4) (domain marked in black) at its N-terminus and an N-terminus motif (SEQ ID NO: 5) ($SP_{1-7}$; dark grey). (1B) Putative trypsin/chymotrypsin cleavage sites of the full length DrmSP amino acid sequence. Trypsin, 6 putative sites (upward arrow); Chymotrypsin 1, 6 putative sites (dumbbell); Chymotrypsin 2, 9 putative sites (downward arrow); extracted from: Peptide Cutter; http://delphi.phys.univ-tours.fr/Prolysis/cutter.html.

It has been found in accordance with the present invention that mating induces proteolytic activity in *D. melanogaster* female hemolymph, affecting the fate of seminal fluid components transferred to the female post-mating. In the examples below we disclose that trypsin activity is present in the hemolymph of mated females and show that it efficiently cleaved T-SP in a distinct pattern. Although unmated female hemolymph also cleaved T-SP, it was much less efficient and with cleavage pattern different from that produced by mated female hemolymph. Our results suggest that mating up-regulates trypsin activity in the female hemolymph. This trypsin may be either male-derived or female endogenous.

We have shown that cleavage at a scissile bond within the N-terminus $K_8$) liberates 2 biologically active fragments while cleavage at a scissile bond within the C-terminus ($R_{25}$-$L_{26}$) inactivates DrmSP's ability to exert its effect on female remating. The disulphide bridge ($C_{24}$-$C_{36}$) that forms a loop at the C-terminal of DrmSP probably represents a specific configuration needed for DrmSP-receptor interaction. A change in this spatial arrangement may lead to a change in the bioactivity of DrmSP. Disruption of C-C bridge by trypsin would allow the two regions, which are normally linked, to separate and it is likely that the resulting change in the configuration may underlie the loss of bioactivity. Thus, this specific spatial arrangement of DrmSP is necessary for its optimal biological activity, the maintenance of the post-mating behavioural response of the female. Accordingly, we infer that this process is part of a female "strategy" to shorten the period of male-induced constraint on female receptivity.

It has also been found in accordance with the present invention that abolishment of trypsin cleavage sites in the DrmSP prolongs the female non-receptivity to further mating. Proteins and peptides are generally cleared from the female hemolymph by proteolytic cleavage; therefore, conceptually, the half-life in the female hemolymph of any peptide expressed in the accessory glands of a male insect and transferred to a female may be prolonged by abolishment of protease cleavage sites in the peptide. In this way, deleterious effects on, for example, the female reproductive system may be prolonged by using the male as a species specific vector.

Thus, the present invention relates, in one aspect, to an isolated nucleic acid molecule comprising, or consisting of, a polynucleotide sequence encoding an oligopeptide capable of inducing post-mating depression of receptivity to mating in female insects, wherein said oligopeptide is resistant to proteolytic degradation.

The terms "oligopeptide capable of inducing post-mating depression of receptivity to mating in female insects", "non-degradable sex peptide", proteolysis-resistant peptide" and "mutated sex peptide" are used interchangeably herein. The terms "proteolytic degradation" and "proteolytic cleavage" are used interchangeably herein.

In one embodiment, the isolated nucleic acid molecule comprises, or consists of, a polynucleotide sequence encoding an oligopeptide derived from the *Drosophila melanogaster* sex peptide ("DrmSP") or from an active fragment thereof, said oligopeptide being modified such as not being degraded by proteolytic enzymes. The wild-type DrmSP has the amino acid sequence set forth in SEQ ID NO: 1, encoded by the nucleotide sequence of SEQ ID NO: 6, and consists of the N-terminal signal peptide of the amino acid sequence as set forth in SEQ ID NO: 4, the N-terminal motif of the amino acid sequence as set forth in SEQ ID NO: 5, and the C-terminus of the amino acid sequence as set forth in SEQ ID NO: 3 (FIG. 1A), The term "active fragment" is used herein to describe a fragment or fraction of a peptide that has equal or substantially similar activity to that of the original complete peptide from which the active fragment was derived.

In another embodiment, the isolated nucleic acid molecule comprises a polynucleotide sequence encoding an oligopeptide derived from the oligopeptide as set forth in SEQ ID NO: 7, comprising the N-terminal signal peptide of DrmSP of the amino acid sequence as set forth in SEQ ID NO: 4 linked at its C-terminus to an amino acid sequence derived from the C-terminal amino acid sequence of DrmSP as set forth in SEQ ID NO: 3. This truncated peptide (FIG. 1A; $SP_{8-36}$) does not contain the N-terminus of SEQ ID NO: 5 and is the longest DrmSP fragment that stimulates non-receptivity (Schmidt et al. 1993).

The N-terminal tryptophan rich motif has been shown to up-regulate in vitro synthesis of juvenile hormone III-bisepoxide ($JHB_3$) in the functionally immature corpus allatum (CA) of female *D. melanogaster*, leading to enhanced oogenesis. The priming effect of the DrmSP N-terminal motif occurs only until the CA attains functional maturity some days after adult female emergence. This effect occurs in other insects too: It is essential for stimulating the CA of the moth *Helicoverpa armigera*, whereas an analogous *D. melanogaster* peptide—Ductus ejaculatorius peptide (Dup 99B), lacking the distinctive N-terminal, does not. We found that the DrmSP N-terminus motif is absent in the deduced amino acid sequence of *C. capitata* and that the DrmSP with its N-terminal motif unexpectedly depresses in-vitro synthesis of $JHB_3$ by the CA of young unmated female *C. capitata*. Thus, its N-terminal motif appears to be antagonistic to JH production in *C. capitata* and therefore, a non-degradable sex peptide molecule, which either inhibits $JHB_3$ synthesis or has no effect on the CA, impose long-term non-receptivity in *C. capitata*, decrease female oviposition and potentially interfere with other JH-depended processes.

Also included in the scope of the present invention are peptides intended for use in species where the N-terminal tryptophan rich motif up-regulates synthesis of $JHB_3$, wherein the peptides are sex peptides lacking this N-terminal motif, and fused peptides, wherein peptides that in certain species negatively affect female reproductive traits, such as CA maturation, oogenesis and pheromone production, are linked to the mutated sex peptide sequence.

Also encompassed within the scope of the invention are isolated nucleic acids molecules which differ from the nucleic acid molecules of the invention due to degeneracy of the genetic code.

The oligopeptides encoded by the nucleic acid molecules of the invention are not limited to those defined herein by specific amino acid sequences but may also be variants of these oligopeptides or have amino acid sequences that are substantially identical to those disclosed above. A "substantially identical" amino acid sequence as used herein refers to a sequence that differs from a reference sequence by one or more conservative or non-conservative amino acid substitutions, deletions, or insertions, particularly when such a substitution occurs at a site that is not the active site of the molecule, and provided that the polypeptide essentially retains its functional properties. A conservative amino acid substitution, for example, substitutes one amino acid with another of the same class, e.g., substitution of one hydrophobic amino acid with another hydrophobic amino acid, a polar amino acid with another polar amino acid, a basic amino acid with another basic amino acid and an acidic amino acid with another acidic amino acid. One or more amino acids can be deleted from the peptide, thus obtaining a fragment thereof without significantly altering its biological activity.

The term "variant" as used herein refers to polynucleotides or polypeptides modified at one or more base pairs, codons, introns, exons, or amino acid residues, respectively, yet still retain the biological activity of a polypeptide of the naturally occurring sequence.

The present invention further relates to an isolated nucleic acid molecule comprising a polynucleotide sequence encoding an oligopeptide that has an amino acid sequence that is at least 80%, at least 85%, at least 90%, or at least 95, 96, 97, 98, or 99% identical to the amino acid sequence of SEQ ID NO:1 or SEQ ID NO: 6. These oligopeptide variants have equal or substantially similar activity to the oligopeptide of SEQ ID NO: 1 and SEQ ID NO: 7. In these variants, the up to 20% difference in the sequence occurs among those amino acid residues that are not modified to bestow resistance to degradation by proteolytic enzymes.

In a preferred embodiment, the isolated nucleic acid molecule according to the invention encodes an oligopeptide made resistant to proteolytic degradation by trypsin due to the abolition of at least one trypsin cleavage site present in the oligopeptide of SEQ ID NO: 3 by conservative substitution of at least one arginine residue and/or at least one lysine residue.

For the purpose of the present application the term "oligopeptide resistant to proteolytic degradation" means an oligopeptide that the degradation of 50% of which takes more than about 20 minutes after being contacted with mated female hemolymph or less than 50% of which is degraded after 1 hour.

A neutral or conservative substitution or mutation as used herein refers to replacement of an amino acid residue by an amino acid which is chemically similar to the replaced amino acid, such that no appreciable effect on the activity of the protein or peptide is expected and the protein or peptide may still function normally. The oligopeptides carrying the conservative substitution or mutation are also referred herein as "mutated peptides".

The rationale for replacing lysine and/or arginine by conservative substitution is that the protease trypsin cleaves exclusively C-terminal to arginine and lysine residues. Thus, replacing lysine and/or arginine by, for example, glutamine, renders the peptide resistant to proteolysis by trypsin while conserving the physical properties of the amino acid residue replaced.

In a more preferred embodiment, the at least one arginine residue and/or at least one lysine residue is substituted with a glutamine residue.

In one embodiment, the isolated nucleic acid molecule of the invention comprises a polynucleotide sequence encoding the oligopeptide as set forth in SEQ ID NO: 8, wherein Arg25 of SEQ ID NO: 3 of the DrmSP is substituted by glutamine.

In preferred embodiments, the isolated nucleic acid molecule comprises the polynucleotide sequence as set forth in SEQ ID NO: 9 encoding the oligopeptide comprising the amino acid sequence set forth in SEQ ID NO: 8, wherein Arg25 of SEQ ID NO: 3 is substituted with glutamine, or the isolated nucleic acid molecule comprises the polynucleotide sequence as set forth in SEQ ID NO: 10 encoding the oligopeptide comprising the amino acid sequence set forth in SEQ ID NO: 11, wherein Arg25 is substituted with glutamine.

The numbering of the amino acid residues comprising the DrmSP peptides begins at the N-terminus of the mature peptide consisting of the N-terminal motif and the truncated C-terminal peptide (see FIG. 1A), such that, for example, arginine at position 25 from the N-terminal of the mature peptide is referred to as Arg25 also in a fragment of the full length peptide such as the truncated C-terminal.

As shown herein below, the peptide having the sequence MKTLALFLVLVCVLGLVQAKPTKF-PIPSPNPRDKWCQLNLGPAWGGRC (SEQ ID NO: 9) was effective in prolonging the post-mating behavior of the transgenic females expressing the peptide. This peptide lacks the DrmSP N-terminal motif, WEWPWNR, (SEQ ID NO: 5), which inhibits JHB3 synthesis in certain species such as *C. capitata*. Thus, a full-length DrmSP variant comprising SEQ ID NO: 8 and the DrmSP N-terminal motif, having the sequence MKTLALFLVLVCVLGLVQAWEWPWN-RKPTKFPIPSPNPRDKWCQLNLGPA WGGRC (SEQ ID NO: 11), would adversely affect additional parameters of insect female fitness, further improving SIT.

The present inventors have previously shown that DrmSP can markedly and significantly reduce the specific synthesis of IHB3 in *C. capitata* (Moshitzky et al., 2003) and that *Drosophila melanogaster* sex peptide stimulates juvenile hormone synthesis which leads to depression of sex pheromone production in *Helicoverpa armigera*, insects of a different order (Fan et al, 1999; 2000).

Therefore, in accordance with the present invention, the female insect may be a member of an order of insects selected from the group consisting of Anoplura, Hemiptera, Holometabola, Coleoptera, Diptera, Hymenoptera, Lepidoptera, Mecoptera, Megaloptera, Neuroptera, Siphonaptera, Strepsiptera, Trichoptera, Mallophaga, Psocoptera, Thysanoptera, Orthoptera, Blattaria, Dermaptera, Embioptera, Grylloblattodea, Isoptera, Mantodea, Mantophasmatodea, Plecoptera and Zoraptera.

In preferred embodiments, the insect is a member of the Lepidoptera order, in particular of a genus in the Noctuidae family selected from the group consisting of Helicoverpa, Heliothis and Pseudaletia such as, but not limited to, *Helicoverpa armigera*.

In a more preferred embodiment, the insect is a member of the Diptera order, more preferably the insect is a member of a family selected from Tephritidae, Drosophilidae, and Culicidae, such as, but not limited to *Ceratitis capitata* of the Tephritidae family, *Drosophila melanogaster* of the Drosophilidae family or a member of the Anopheles genus of the Culicidae family.

In a most preferred embodiment, the insect is *Ceratitis capitata*.

In accordance with the present invention, the non-degradable sex peptide trait is preferably expressed in males that are sterile. The two traits may be obtained by either irradiating transgenic males of the invention expressing a mutant polynucleotide molecule encoding for a mutated sex peptide or by expressing the mutant sex peptide in an insect strain carrying one or more repressible or inducible mutant genes causing infertility. The repressible genes causing infertility can be repressed by an external additive, which allows the insects to be reared in manufacturing facilities. This external additive is commonly administered orally, for example as an additive to the insect food. The inducible genes may be induced only in the male insects intended for release.

Another strategy is to produce two fertile transgenic strains that when crossed produce infertile offspring. The insects can also be given genetic markers, such as fluorescence, that make monitoring the progress of eradication easier.

In another aspect, the invention relates to an expression vector comprising the nucleic acid molecules encoding for the mutated sex-peptides of the invention, wherein the nucleic acid molecule is operably linked to a promoter inducible by a transcription factor and to a terminator.

The term "expression vector" as used herein refers to a vector, also known as an expression construct or a plasmid, that has been designed to express cloned genes in a particular cell type. The plasmid is engineered such that it contains a highly active promoter which causes the production of large amounts of mRNA. The term "transcription factor" is used herein to describe a DNA binding transcription regulator or non-DNA transcriptional co-regulator that can activate or repress transcription, and a "transcriptional activator" is a transcription factor that can only activate transcription. Without transcription factors, the creation of new RNA from DNA cannot occur. The specific binding site of the transcription factor on the DNA is referred to as a promoter, a regulatory region of DNA located upstream or downstream (towards the 5' or 3' region of the sense strand, immediately adjacent to, or physically distant from, the transcribed region) of a gene that allows transcription of the gene.

In one embodiment, the inducible promoter is substantially inactive in the absence of said transcription factor. This is important because expression of the mutated sex peptide at inappropriate times will reduce the fertility and thus the production rate of the insects. The transcription factor may be an endogenous transcription factor inducible, for example, by external or developmental signals that enable expression of the mutated sex peptide only at the appropriate developmental stage and in the appropriate tissue, or preferably it may be a non-endogenous transcription factor that may be encoded on a separate expression vector from the vector encoding the sex peptide. The non-endogenous transcription factor is preferably the yeast transcription factor, or transcriptional activator, GAL4, but may be any transcription factor that is not naturally expressed in the insect.

In one embodiment of the present invention the expression of the transcriptional activator GAL4 is controlled by an accessory gland specific promoter, thus ensuring expression of GAL4 only in accessory glands.

In a preferred embodiment, the accessory gland specific promoter 26Aa is used as an endogenous enhancer that controls the expression of GAL4. On a separate plasmid, the gene encoding for a mutated sex-peptide of the invention is under the control of UAS and is therefore expressed only in the presence of GAL4 which is expressed only in accessory glands.

In the GAL4 system (Brand and Perrimon, 1993), a cell-type specific cloned promoter or endogenous enhancer directs the expression of the yeast transcriptional activator GAL4 in a spatially restricted fashion. The construct carrying the promoter or enhancer and the GAL4 gene is termed "driver vector" and the line of insects carrying this construct is termed "driver line". On a separate plasmid, or expression vector, termed the "target vector", a binding sequence specific for the transcriptional activator GAL4 (the upstream activating sequence, UAS) directs the expression of a transgene, in fact acting as a promoter. The line of insects carrying this construct is termed "target line". Conditions that allow for the expression of GAL4 may thus induce the expression of any gene of interest that has been cloned downstream of a UAS binding site. The advantage of this system is that the transcriptional activator and the UAS-based transgene are carried in different parental lines, thus ensuring their viability and enabling a combinatorial approach with different driver and target lines to the biological question of interest. The GAL4 transcription factor system may be also utilized within more complex systems that allow for both spatial and temporal control of the expression such as the Gene-Switch, and TARGET systems (McGuire et al., 2004).

The invention further relates to a transgenic insect comprising the isolated nucleic acid molecule or the expression vector(s) according to the present invention.

As mentioned above, the non-endogenous transcription factor is preferably a non-endogenous transcription factor that may be encoded on a separate expression vector from the vector encoding the sex peptide. This enables rearing two separate strains of insects; one which carries the mutated proteolysis-resistant sex peptide on one expression vector and the other which carries GAL4 on a second expression vector. Both strains are fully fertile and large numbers of insects may be produced. In order to produce the transgenic male that expresses the mutated sex peptide, the two strains are crossbred and the offspring, which carries both genes, is capable of expressing the mutated sex peptide.

Thus, in one most preferred embodiment of the present invention, the transgenic insect comprises a first expression vector comprising the nucleic acid sequence encoding the mutated sex peptide and a further expression vector comprising a polynucleotide encoding a non-endogenous transcription factor capable of inducing the promoter to which the polynucleotide is operably linked, wherein said non-endogenous transcription factor is capable of inducing the expression of the nucleic acid comprised within the first expression vector.

In preferred embodiments, the non-endogenous transcription factor is the transcriptional activator GAL4 and said promoter is an accessory gland specific promoter such as the 26Aa promoter.

The transgenic insect may be at any developmental stage such as a fertilized egg, the larval stage, the pupal stage or a mature adult.

In a preferred embodiment, the transgenic insect is a male pupa or a sexually mature male adult, more preferably sexually sterile, and the nucleic acid encoding for the mutated sex peptide of the invention is functionally expressed in cells of the retrogonadal complex, also termed gonadal glands, accessory glands or paragonia.

In one embodiment, the transgenic insect is sexually sterile as a result of irradiation or as a result of said male expressing genes causing sterility.

In a preferred embodiment, the transgenic insect is sexually sterile as a result of irradiation.

In more preferred embodiments, the transgenic insect comprises the polynucleotide sequence as set forth in SEQ ID NO: 9 encoding for the oligopeptide comprising the amino acid sequence set forth in SEQ ID NO: 8, wherein Arg25 is substituted by glutamine or the nucleotide sequence as set forth in SEQ ID NO: 10 encoding for the polypeptide having the amino acid sequence as set forth in SEQ ID NO: 11, wherein Arg25 of the DrmSP is substituted with glutamine, and said insect is an irradiated sexually sterile pupa or mature male adult.

In a further aspect, the invention provides a method for controlling a population of insects in a natural environment comprising releasing male transgenic insects according to the invention into the environment at a locus for insect population control.

The present invention addresses a significant part of the important problems associated with presently used "Sterile Insect Techniques", since its purpose is to generate insect males with non-degradable (persistent over time) sex peptide (SP), and the possibility of disrupting female fertility by introducing the N-terminus of *Drosophila melanogaster* SP into female insects to derange egg production.

It is important to note that the transgenic males of the invention transferring to female mates a sex peptide resistant to proteolytic degradation are designed to impose non-receptivity and reduced fertility on the females they have mated with, persisting long after these transgenic males have died. Thus, a procedure according to the present invention could markedly reduce the number and frequency of release of sterile males.

The currently existing methods for biological control of insects, particularly the fruit fly, Ceratitis capitata, comprise releasing into the environment sterile male insects. The female insects are not fertilized after mating with the sterile male or a transgenic male such as disclosed in WO01039599, but are able to mate again with fertile male in their environment and produce progeny. In addition, under normal circumstances, unmated females, or females that have mated with such sterile males, produce infertile eggs at a reduced rate, but they continue to deposit eggs in fruit.

The method of the present invention is fundamentally different from these current methods, since it is not directed to improve the sterile trait of the male insect as is for example the "lethal gene" method mentioned above and disclosed in WO01039599, but is instead directed to prolonging the "sterile", i.e. the non-receptive period, of the female. A wild-type female that has mated with a sterile male according to the present invention is prevented from mating with fertile wild-type males long after the infertile male has died and its oogenesis and egg deposition is deranged.

The invention will now be illustrated by the following non-limiting examples.

EXAMPLES

Materials, Methods and Experimental Design.

Materials. The chromogenic trypsin and chymotrypsin substrates: N-Benzoyl-DL-Arg-p-Nitroanilide (N-Bnz-R-pna), N-Benzoyl-L-Tyr-p-Nitroanilide (N-Bnz-Y-pna), N-Benzoyl-Phe-Val-Arg-p-Nitroanilide (N-Bnz-FVR-pna), N-B enzoyl-Pro-Phe-Arg-p-Nitroanilide (N-Bnz-PFR-pna), and the trypsin and chymotrypsin inhibitors: Bowman-Birk inhibitor (BBI), Na-p-Tosyl-L-lysine chloromethyl ketone hydrochloride (TLCK), were purchased from Sigma-Aldrich (Rehovot, Israel). The elastase substrates: N-Succinyl-Ala-Ala-Ala-pna (N-Suc-AAA-pna), N-Succinyl-Ala-Ala-Pro-Leu-pna (N-Suc-AAPL-pna), were purchased from Sigma-Aldrich (Rehovot, Israel). N-Succinyl-Ala-Ala-Val-pna (N-Suc-AAV-pna), N-Succinyl-Ala-Ala-Pro-Ile-pna (N-Suc-AAPI-pna) were purchased from Bachem (Bubendorf, Germany). The subtilisin substrate: Z-Gly-Gly-Leu-p-Nitroanilide (Z-GGL-pna) was purchased from Sigma-Aldrich (Rehovot, Israel).

Trypsin from bovine pancreas, α-Chymotrypsin from bovine pancreas, Elastase from porcine pancreas and Subtilisin A from *Bacillus licheniformis* were purchased from Sigma-Aldrich (Rehovot, Israel).

N-terminal truncated DrmSP (DrmSP$_{8-36}$, T-SP) was custom-synthesized by the organic chemistry peptide synthesis facility of the Weizmann Institute of Science (Rehovot, Israel).

Fly stocks. The Canton-S strain of *D. melanogaster*, transgenic stocks for UAS-DrmSP$_{TSP}$ which are described below, hsp70-GAL4_CyO stock (Brand and Perrimon, 1993) and Acp26Aa-P-Ga14 stock (Chapman et al. 2003) were kept at 25±2° C. and a 12:12 (light:dark) photoperiod on semi-defined media (Backhaus et al., 1984). For experiments wherein hemolymph from unmated females was collected: unmated females were separated from males immediately after eclosion; if hemolymph of mated females was collected: mated females were grouped with males immediately after eclosion and aged together for 4 days after which they had all mated. In experiments were mating must be controlled was a single unmated female placed in a food vial with a single unmated 3-5-day-old male.

Hemolymph sample preparation. Hemolymph from batches of 250 unmated or mated females was extracted 4 days after eclosion as in Lung and Wolfner (1999). Briefly, groups of 5 flies, punctured in the prothorax, were placed head down in chilled Eppendorf tubes (0.5 ml tube pierced in the bottom and inserted into intact 1.5 ml tubes) and centrifuged at 4° C. Tubes were inspected for presence of fat body. Ten μl of 100 mM Tris buffer, pH 8.0, was added to the first tube, and then the collected hemolymph plus Tris from tube 1 was transferred from this tube to the next tube and so on, in to pool hemolymph extracted from unmated or mated female flies.

SDS polyacrylamide gel electrophoresis (SDS-PAGE) and Western blots. Hemolymph samples were collected and pooled as above (section 2.3), added to 20 μl of homogenizing buffer and an equal volume of SDS-PAGE sample buffer (Monsma and Wolfner, 1988). Samples were boiled, and then frozen at −20° C. until loading. SDS-PAGE was done on 15% polyacrylamide gels and Western-blotted as in Lung and Wolfner (1999). Proteins were cross-linked to the filter to aid in the retention of Sex peptide. Primary anti-DrmSP C-terminal antibody (kindly provided by E. Kubli; Zurich, Switzerland) was diluted 1:750 in blocking solution; donkey anti-rabbit secondary antibody conjugated with horseradish peroxidase (Sigma) was diluted 1:10000 in blocking solution. Proteins were visualized using an enhanced chemiluminescence (ECL) detection system (Amersham).

HPLC of T-SP incubated with unmated or mated female hemolymph. Incubations were performed with hemolymph of 20 female-equivalents per reaction, in the presence of 2 mM dithiothreitol (DTT) and 17 μg of synthetic T-SP. Reaction mixtures were incubated at 37° C. for various time intervals (0, 15, 30 and 60 min). To precipitate the proteins and terminate the reaction, ice-cold methanol was added to a final concentration of 80%. Samples were placed on ice for 10 min and then centrifuged for 5 min at 10,000 rpm at 4° C. The supernatant was transferred to a new tube and vacuum-dried. Samples were run on a LaChrom Merck Hitachi HPLC using C18 columns (Lichrospher® 100; RP-18, 5 μm) in the presence of 0.01% trifluoroacetic acid (TFA). Elution was performed at a flow rate of 1 ml/min with the following sequence: 10 min isocratic at 0% acetonitrile; 5 min with a gradient to 20% acetonitrile; 40 min with a gradient to 40% acetonitrile. In order to calculate degradation rates, the value at $T_0$ was taken as 1, while at subsequent time points the integral of the residual T-SP was calculated as fractions of $T_0$.

Liquid Chromatography—Mass Spectrometery (LC-MS/MS). Hemolymph was prepared as described in section 2.3, except that 50 *D. melanogaster* female-equivalents of unmated or mated female flies were used for 30 min incubations with 20 μg of T-SP. Reactions were terminated and processed as detailed in section 2.5. The supernatants of the methanol precipitations were lyophilized and resuspended by sonication in 100 μl of loading buffer (5% acetonitrile, 0.1% formic acid) and analyzed by LC-MS/MS. Briefly, the peptide mixtures were run in an Agilent 1100 series micro-flow HPLC system (Agilent Technologies, Inc., Palo Alto, Calif.) coupled to an Esquire-HCT ion trap mass spectrometer through the online nano-ESI ion source (Broker Daltonik GmbH, Bremen). Peptides were separated on a Protein-15-C18-150 microbore column (Micro-Tech Scientific, Cousteau, Court Vista, Calif.) using a 5% to 30% gradient of acetonitrile in 0.1% formic acid for 37 min at 250° C., at a flow rate of 1 μl/min. MS and MS2 spectra were acquired in a data-driven way with parameters optimized for peptide mixture analysis. The resulting MS/MS chromatograms were processed by the DataAnalysis 3.1 application and further analysed with BioTools 2.2 (Broker Daltonik GmbH, Bremen) and MASCOT (Matrix Science), assuming the unknown specificity of the hemolymph protease. A 95% confidence interval was set as threshold.

Protease and inhibition assays. Protease activity in *D. melanogaster* female hemolymph was assayed using chromogenic substrates. N-Bnz-R-pna, N-Bnz-Y-pna, N-Bnz-F'VR-pna, N-Bnz-PFR-pna, N-Suc-AAV-pna, and N-Suc-AAPI-pna were all dissolved in DMF, to a 10% final concentration of DMF in the reaction (v/v). Final substrate concentration in the reaction was 1 mM for all except N-Bnz-Y-Pna which was 0.5mM and Z-GGL-pna which was 0.2 mM. N-Suc-AAA-pna was dissolved in DMSO, to a 10% final concentration of DMSO in the reaction (v/v). Final concentration in the reaction was 0.1 mM. N-Suc-AAPL-pna was dissolved in 25% DMF/75% of 100 mM Tris pH 8.0, to a 2.5% final concentration of DMF in the reaction. Final concentration in the reaction was 1 mM. DTT concentration was 2 mM in the reaction mixture. DTT was added to provide a possible requirement of a reducing environment for the serine proteases.

Commercial enzymes (response controls of the specific reaction mixture) were dissolved in 100 mM Tris buffer, pH 8.0, at a concentration of 5 μg/μl. Serial dilutions were used to create a standard curve. Assays were performed in 96-well plates (Nunc, Roskilde, Denmark) in a final volume of 250 μl. Incubations at 37° C. were performed in a shaker incubator (Heidolph, Essex, England). Prior to reaction with hemolymph proteases, reaction mixtures were temperature-equilibrated with buffer±2 mM DTT, and substrate. Reaction was initiated by addition of substrate and terminated after 60 min at 37° C. by addition of acetic acid to a final concentration of 6%. Activity was recorded as increase in absorbance, due to the release of 4-nitroaniline, as measured using an ELISA reader with 405 nm filter in an ELISA Plate Reader (ELx800, Bio-Tek Instruments). Values are relative absorbance readings, obtained with equal fly-equivalents of hemolymph as source of protease. Hemolymph was extracted from 4-days old mated females, at which age and physiological state putative enzymatic activity is assumed to be highest. Hemolymph protein content was measured spectroscopically at 280 nm, and was 0.5-1 μg per female. For all assays, acquired raw data were processed by subtracting background from experimental values to yield an absolute value representing the net chromogenic response due to enzyme activity on the substrate.

For inhibition assays of trypsin, the reactions were performed in a similar manner, using N-Bnz-R-pna as the substrate, except for an additional pre-incubation for 20 min with 25 μl of BBI (5 μM final concentration in the reaction, prepared in reaction buffer) or TLCK (1 mM final concentration in the reaction, prepared in reaction buffer). All incubations were performed at 30° C. and all assays were repeated 3 times in triplicates.

Transgenic flies. The GAL4-UAS system, first described by Brand and Perrimon (1993), was used for transgenesis of *D. melanogaster*. Briefly, T-SP was cloned into the pUAST vector, which bears an upstream activating sequence (UAS) site able to bind to the yeast transcription factor GAL4. Two separate fly lines are reared, the one (UAS) bearing the gene(s) to be transcribed and a chosen promoter (target line), the second being the GAL4 activating line. By select and controlled crossing of these two parent lines, the transgene, in this case T-SP or its amino-acid substituted homolog, is activated and expressed in the filial generation, at different times during development, and/or in select tissues, dependent on the promoter and inducer utilized. In this case, the GAL4 gene is under the control of the accessory gland specific promoter 26Aa that is induced only in the accessory glands (Park et al., 1994).

We constructed a T-SP clone including the N-terminal signal sequence and the truncated C-terminal, but lacking the N-terminal motif (SEQ ID NO: 5). To express T-SP resistant to degradation we constructed mutant clones that are intended to be non-degradable when transcribed in vivo. The reason for the choice of a partial T-SP sequence instead of a mutant in the full-length sequence of DrmSP is to prevent the concomitant up-regulation of JH biosynthesis by the N-terminus of DrmSP in the transgenic flies, which might confuse the physiological response leading to control of behavior. Using oligonucleotide cloning, we substituted arginine at position 25, with glutamine, to eliminate the possible tryptic cleavage site.

The modified oligos were cloned into pUAST by means of NotI/XbaI sites. We added the DrmSP signal sequence (amino acids 1-18) to the N terminus of DrmSP$_{TSP}$ to allow secretion. The signal sequence was cloned into pUAST by means of EcoRI/NotI sites. Restriction enzyme digestion and sequencing confirmed that the mutant fragments inserted in the predicted position near the 3' end of the UAS elements.

In order to enable expression also in non-accessory gland tissue and independently to the presence of GAL4 and in order to confer temporal control of the expression, for example in transgenic unmated female flies, the heat-shock regulated promoter Hsp 70 was inserted upstream to the T-SP sequence.

Generation of transgenic lines by microinjection into w1118 embryos was performed by using standard methods (Klemenz et al., 1987). Briefly, eggs deposited by reproductively mature females, 4-6 days after eclosion, were collected hourly and used for injection during the following half-hour, prior to formation of pole cells. Injection into the embryo was performed on dechorionated eggs in a temperature and humidity-controlled room at 20° C. Larvae hatched 24 after injection were placed individually on the agar-based diet in test tubes for 10 days. Adult emerged (white-eyed flies), were sexed and kept separately. Three-four days later they had reproductively matured, and were individually mated with $w^{1118}$ male or female adults accordingly. Ten days later, the filial generation adults were examined. Red eyes indicate a transgenic adult. Intra-line red-eyed transgenic adults (heterozygous flies) were mated for several generations to verify that the population was homozygous, before bioassaying.

TABLE 1

List of wild-type and mutant amino acid sequences in DrmSP$_{TSP}$ mutants

| Mutant designation | Amino acid sequence | SEQ ID NO: |
|---|---|---|
| T-SP | KPTKFPIPSPNPRDKWCRLN LGPAWGGRC | SEQ ID NO: 3 |
| Q | KPTKFPIPSPNPRDKWCQLN LGPAWGGRC | SEQ ID NO: 12 |

Substituted amino acid is in bold:
Q - Substitution of amino acid R with Q in position 25;

Heat shock. Transgenic unmated females carrying the mutated T-SP (hsp70-GAL4; UAS-T-SP$_X$) were placed in empty vials supplemented with moisture filter paper. Files were placed in water bath and heated gradually from 25 to 37° C. Flies were kept at this temperature for 1 hr thereafter returned to room temperature for one hour for recovery. Recovered heat-shocked flies were placed in food vials and kept at 25° C. until used.

RT-PCR. Expression was induced by a heat-inducible GAL4 driver (hsp70-GAL4), or with the Acp26Aa GAL4 driver (Acp26Aa-GAL4) which, restricts expression to the male accessory glands exclusively. To verify the expression of T-SP, groups of 10 heat-shocked females were taken at different time post-heat-shock, placed in Eppendorf tubes, quick-frozen in liquid nitrogen and kept at −80° C. until subject to RNA extraction. mRNA extraction was performed with Dynabeads (Invitrogen) according to the manufacturer's instructions.

cDNA of the total message in the whole body preparation was obtained with the SuperScript III first strand Synthesis system for RT-PCR (Invitrogen) and an oligo-dt primer. PCR was performed on the single strand obtained with 26 cycles for the T-SP transgenes: T-SP and T-SP$_O$. Products were run on agarose gels and stained with ethidium bromide. For a positive control we used DrmSP cDNA. To quantify the amount of T-SP produced in the different transgenes we used Image that measured the intensity level of T-SP bands visualized by ethidium bromide.

Receptivity assay. Single unmated females of each homogenous UAS-T-SP transgene (see also Table 2) were placed in a food vial with single unmated 3-5-day-old males of the same UAS-T-SP transgene. Two parameters were monitored for one hour: (i) Receptivity rate—the number of female that mated; (ii) courtship behavior—whether or not female performed a rejection behaviors (kicking and extruding their ovipositor). If the female exhibited one of the above behaviors she got a score of 0.5, no such behaviors she got a score of 0. For that a group of 10 females were isolated from each group and their behavior was inspected. Females that do not mate by the end of this period are regarded as non-receptive. These females will be exposed in the next day to newly unmated 3-5-day-old males (see section developing bioassay for additional details).

Example 1

Full Length DrmSP can be Found in Mated Female Hemolymph

Figure 2:
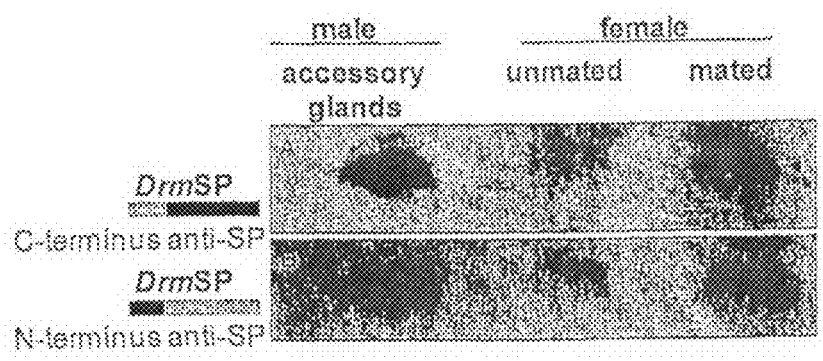
FIG. 2 depicts a Western blot analysis showing that full length DrmSP is transferred to the female hemolymph post-mating. Protein equivalents of 2 males' accessory glands and hemolymph of 250 4-day-old unmated and mated females were loaded in each lane. Antibodies against $SP_{1-36}$ (C-terminus anti-SP) and $SP_{1-7}$ (N-terminus anti-SP) detected one band at the predicted size of DrmSP (indicated by an arrow head).

DrmSP is transferred to the female during mating. After entering the female reproductive tract, it has been assumed that DrmSP enters the hemolymph where it can reach its targets in the central and the peripheral nervous system and markedly affect post-mating female reproductive physiology and behavior (Ding et al., 2003). In addition, a considerable portion of DrmSP in the female has been found in the sperm storage organs, where it is bound to sperm tail by its N-terminus. It has been hypothesized that DrmSP is slowly released over several days, presumably by proteolytic detachment from its binding site, and the residual C-terminal region of DrmSP transfers into the hemolymph, where it prolongs DrmSP effect on female behavior. To address this issue, we first examined if DrmSP does indeed enter the female hemolymph. For this, hemolymph was collected from mated females and compared to control hemolymph of unmated females. To characterize DrmSP in female hemolymph we used two different antibodies: an antibody specific for the fragment SP$_{1-7}$ (AB SP$_{1-7}$) that recognizes only the N-terminus of the molecule and an antibody for SP$_{1-36}$ that recognizes the C-terminus of the molecule. A band in the molecular range of DrmSP is observed in samples of hemolymph from mated female flies and extract from male accessory glands. No immunoreactivity was evident in control hemolymph samples of unmated female flies (FIG. 2). Both antibodies (AB SP$_{1-7}$ and AB SP$_{1-36}$) detected DrmSP in female hemolymph (FIGS. 2A-B). This demonstrates that a discernable amount of full length DrmSP enters the female hemolymph post-mating.

Example 2

Trypsin-Like Activity is Present in the Hemolymph of Mated Female Flies

Figure 1B:
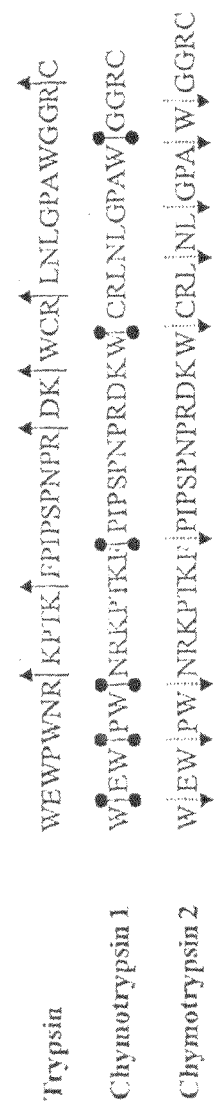

The full-length DrmSP sequence possesses putative cleavage sites of three serine proteases (see FIG. 1B). We hypothesize that DrmSP is subject to proteolysis in female hemolymph, and that this degradation leads to reinstated female receptivity. To identify specific serine protease activity in the hemolymph of mated D. melanogaster females, we used an in vitro assay which utilizes synthetic chromogenic substrates that differentiate among different serine proteases. This approach was selected as it yields a quantifiable measure of enzymatic activity, and can therefore be used to screen for various enzyme activities. For this, newly eclosed D. melanogaster adult flies of both sexes were collected and aged together for 4 days, by which time they had all mated. Extracted mated female hemolymph was incubated with synthetic chromogenic substrates and measurements of released p-nitroanilide were used to quantify enzyme activities. We first examined substrates for trypsin. We found that trypsin activity is present in the hemolymph of mated females (FIGS. 3A-B). These data indicate that all trypsin substrates were effectively cleaved by female hemolymph extracts. The trypsin activity shown by cleavage of the classical substrate (N-Bnz-R-pna) was not diminished by addition of side residues to the enzyme recognition site (N-Bnz-FVR-pna), or the presence of a proline residue (N-Bnz-PFR-pna) (FIGS. 3A-B). This last finding is important because the DrmSP sequence contains several proline residues. The unique structure of proline influences not only the conformation of the peptide chain, but may also restrict the attack of proteases. An addition of DTT greatly enhanced the tryptic activity (e.g. 7 fold for N-Bnz-PFR-pna: from O.D$_{(-DTT)}$=0.17 to O.D$_{(+DTT)}$=1.2; FIG. 3B). A reducing environment has also been shown to activate other insect serine proteases.

The serine protease family also includes subfamilies with different substrate specificities, such as chymotrypsin, elastase, and subtilisin, which could possibly cleave DrmSP. To examine whether such enzymatic activities are also represented in mated female hemolymph, we added to our assay substrates for chymotrypsin 0.15 (N-Bnz-Y-pna), elastase (N-Suc-AAA-pna, N-Suc-AAPL-pna, N-Suc-AAV-pna, N-Suc-AAPI-pna) and subtilisin (Z-GGL-pna). Neither chymotrypsin nor subtilisin activity were evident when assayed with the above substrates (FIG. 3). However, we cannot completely exclude the possibility that these protease activities are absent in hemolymph from mated females since we used only one classical substrate for each enzyme. Although elastase activity was not observed when assayed on its classical substrate (N-Suc-AAA-pna), relatively weak elastase activity was observed on N-Suc-AAPL-pna, N-Suc-AAV-pna and N-Suc-AAPI-pna (FIGS. 3A-B). This may represent activity of other hemolymph proteases with a broad specificity, or minor amounts of elastase-like serine proteases.

Figure 4A:
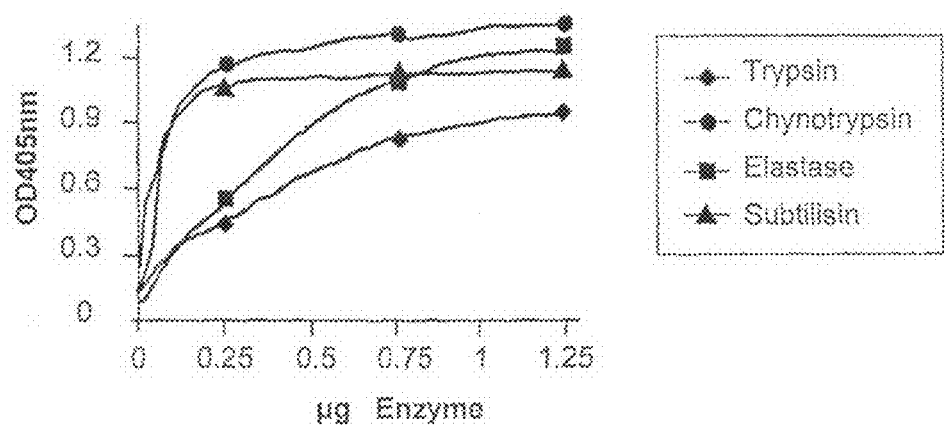
FIGS. 4A-B show that hemolymph extracted from mated females efficiently cleaved trypsin substrate. (4A) Commercially obtained pure enzymes efficiently cleaved synthetic chromogenic substrates of trypsin, chymotrypsin, elastase and subtilisin. (4B) Proteolysis of trypsin substrate (N-Bnz-R-pna) by mated female hemolymph, in the presence of DTT and in the presence of either the specific trypsin inhibitor (TLCK), or the trypsin/chymotrypsin inhibitor (BBI). An absolute value corresponds to the net chromogenic response due to enzyme activity on the substrate. Error bars are means±standard error of means (SEM). Asterisks indicate statistical significance of depressed activity on N-Bnz-R-pna ($p<0.05$). Hemolymph extracted from 250 mated *Drosophila* females, 4-day-old, were used for each assay; all assays were repeated 3 times in triplicates.

To estimate the activity of hemolymph serine proteases in the presence of DTT, commercially obtained pure enzymes were tested to calibrate the system. We assayed trypsin (using N-Bnz-R-pna), chymotrypsin (using N-Bnz-Y-pna), elastase (using N-Suc-AAV-pna), and subtilisin (using Z-GGL-pna). All of the purified enzymes effectively cleaved the substrates used in these experiments (FIG. 4A). We next calculated the presumptive molar equivalent of tryptic activity in mated female hemolymph using the value obtained with bovine trypsin on N-Bnz-R-pna in our in vitro assay system. We found that a value of 0.1 OD units at 405 nm, is equivalent to 0.05 µg of bovine trypsin. Thus, each mated D. melanogaster female contains, on the average, an amount of enzyme in the hemolymph equivalent to 5 ng of trypsin, which translates to 0.2 pmole of catalytically active bovine trypsin.

Figure 4B:
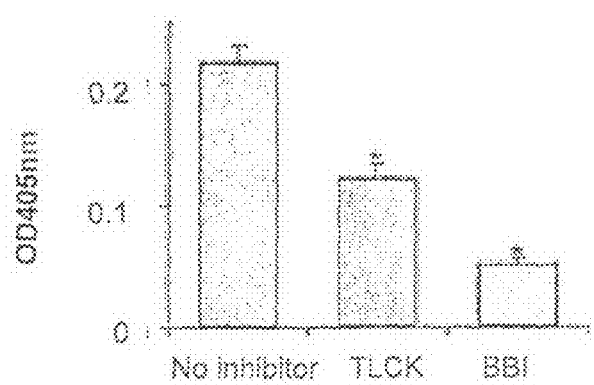

To further confirm that the major enzymatic activity of mated female hemolymph we found was indeed trypsin, we used two specific inhibitors: 1) Bowman-Birk Inhibitor (BBI), a "double-headed" native trypsin/chymotrypsin inhibitor from soybeans, which inhibits trypsin and chymotrypsin in a noncompetitive manner and 2) Na-p-Tosyl-L-lysine chloromethyl ketone hydrochloride (TLCK), a small synthetic compound that inhibits trypsin specifically and irreversibly. Assays were conducted with N-Bnz-R-pna, the classic trypsin substrate. Both inhibitors very significantly reduced cleavage: 40% (in the presence of TLCK (P<0.0005) and 78% in the presence of BBI (P<0.00005) (FIG. 4B).

Together, these results suggest that mated female hemolymph contains trypsin activity which efficiently cleaves DrmSP post-mating. The presence of trypsin susceptible sites within the sex-peptide sequence has also been demonstrated by Peng et al. (2005) who showed that the trypsin cleavage site $R_7K_8$ is essential for release of the C-terminal fragment $SP_{8-36}$ from sperm tail.

Example 3

T-SP Degradation by Mated Female Hemolymph is Much More Rapid and Complete

Figure 5:
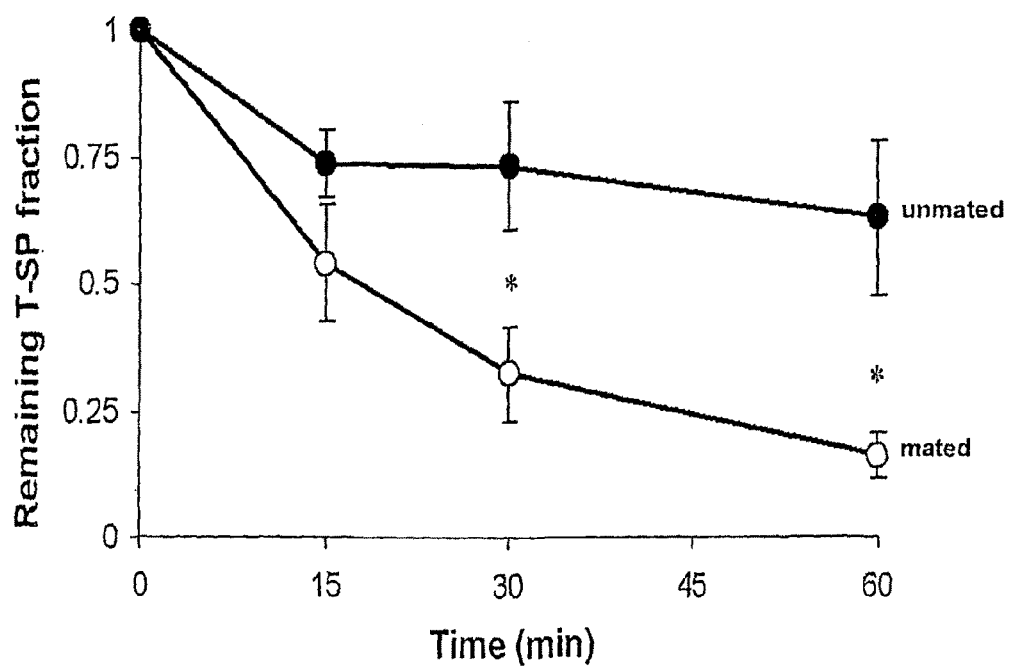
FIG. 5 shows that hemolymph extracted from mated females efficiently degraded truncated sex peptide (T-SP; see FIG. 1A). The residual T-SP fraction after incubation with unmated female hemolymph is shown in filled circles while values obtained for T-SP incubation with hemolymph of mated females is shown in open circles. Values are in means of 3 replicates±standard error of mean (SEM). Asterisks above error bars indicate statistical significance difference of remanning T-SP fraction between unmated and mated female at specific time ($p<0.05$).

After establishing the presence of trypsin activity in hemolymph from mated females, we next questioned whether DrmSP would actually be cleaved by female hemolymph. To examine the pattern of T-SP degradation in mated female hemolymph and compare the ability and pattern with unmated females, we first incubated T-SP with hemolymph extracted from unmated female (see also Material and Methods section 2.5). We found that the rate of T-SP degradation in unmated female hemolymph is low, 25% of the peptide was degraded in 15 min, and thereafter degradation ceased (FIG. 5). However, incubating T-SP with mated female hemolymph degrades 45% of the peptide within 15 min. Degradation of T-SP continued to about 80% within 60 min from the start of the reaction (FIG. 5). Differences in degradation were found to be significant after a 30 min incubation (FIG. 5; p<0.001). These results suggest that the cleavage of DrmSP might be due to an endogenous female protease(s) present at low level in unmated females, whose activity is strongly up-regulated by mating. It is also possible that such protease(s) could be male-derived, transferred to the female during copulation to supplement the endogenous female protease(s).

Example 4

Identification of Major T-SP Scissile Bonds Elicited by Hemolymph Protease

To identify the presumptive endoprotease cleavage sites of T-SP we next used Liquid Chromatography—Mass Spectrometry (LC-MS/MS). The rate of T-SP degradation under defined conditions served as a reference for preparations subjected to LC-MS/MS analysis. T-SP was incubated with mated and unmated female hemolymph for 30 min. The digests were subjected to the LC-MS/MS.

Following 30 min incubation with mated female hemolymph, five fragments were obtained and their sequences aligned against the full length sequence of T-SP (see Table 1 in Pilpel et al. 2008). The first two, generated by cleavage of the T-SP sequence at $R_{25}$-$L_{26}$, are the relatively most abundant fragments, and indicate tryptic activity. The third fragment was obtained in another run only after 40 min incubation and may suggest the presence of minor chymotrypsin-2 or elastase activities. The forth and the fifth fragments probably reflect progressive exopeptidase action, although the forth fragment may also indicate a minor site susceptible to chymotrypsin-1 (see FIG. 1B).

In contrast, T-SP degradation by unmated female hemolymph yielded 11 different fragments, albeit the apparent degree of initial cleavage of the intact T-SP was much less than in mated females (FIG. 5). Although some of the products are the same as those obtained with mated female hemolymph, their abundance is low and other products are also obtained. These may be products of sequential degradation of the two partial peptides by exopeptidases occurring in hemolymph of mated females, or of an array of endo- and exopeptidases present in unmated female hemolymph and depressed in the mated female hemolymph. None of these cleavage products were detected in control runs (i.e. T-SP incubated in buffer without hemolymph).

These results suggest that an array of proteases is present in the hemolymph of unmated and mated females. Moreover, protease activity present in hemolymph of mated females differs from that of unmated females in the dominant site specificity and in the overall level of activity on T-SP. It is possible that proteases present in unmated female hemolymph are essential for the last maturation stage of the reproductive tract pre-mating, but may interfere with seminal fluid activity and thus are immediately down regulated post-mating. Exopeptidases in the hemolymph of both unmated and mated female are undoubtedly involved in second-tier degradation. This might explain the absence of some expected fragments that must have been released but were further degraded to the extent that they were not detectable in this system.

Example 5

Transgenic Lines Carrying Modified T-SP

Figure 6:
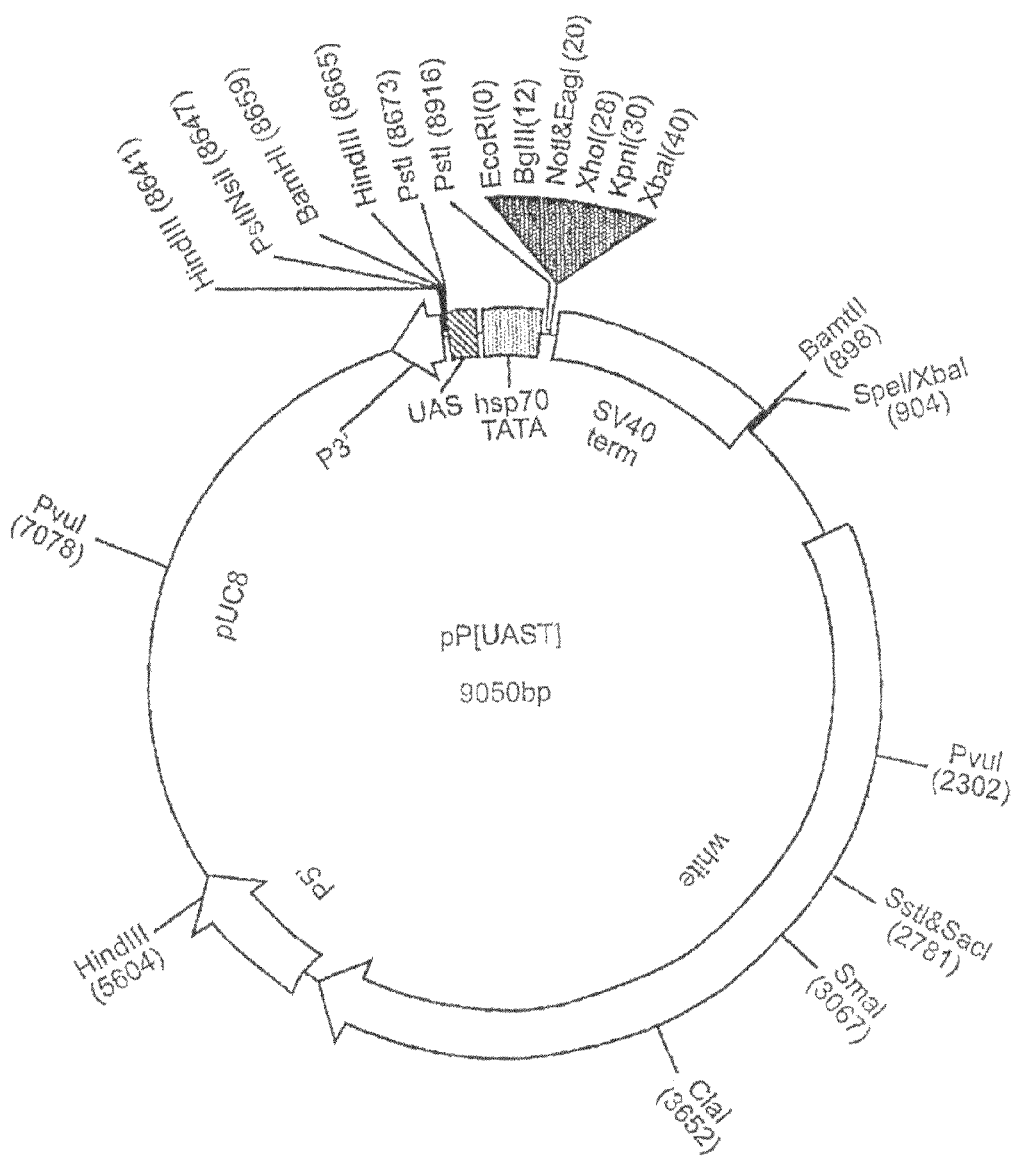
FIG. 6 depicts a schematic portrayal of the pUAST vector. UAS, Upstream Activating Sequence; Hsp70, Heat Shock Protein 70 promoter sequence; Sv40 term, Sv40 terminator sequence.

To examine modified T-SP susceptibility for degradation in vivo we generated two transgenic flies using GAL4-UAS system (FIG. 6). These transgenes were designed for the D. melanogaster model, as "proof of concept". For both T-SP transgenes we obtained more than one line (Table 2). Evaluating more than one line will allow us to eliminate possible position effect due to the integration of the transgene into the genome.

TABLE 2

| DrmSP$_{TSP}$ transgenes | |
|---|---|
| Mutant designation | # of lines |
| T-SP | 3 |
| Q | 10 |

Example 6

Developing Bioassays for Non-Receptivity

Figure 7A:
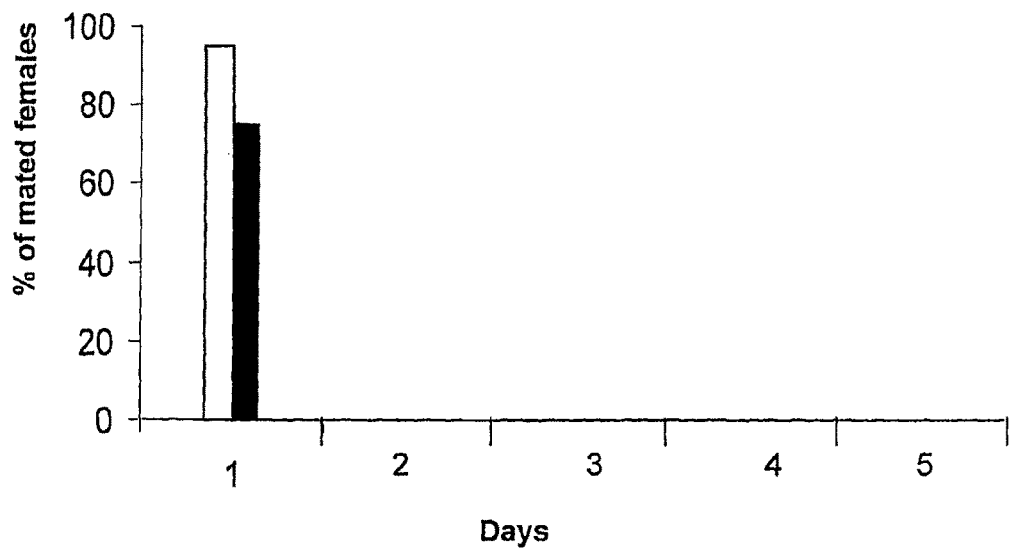
FIGS. 7A-D show graphs indicating that mated females are non-receptive for 4-5 days post-mating.
Figure 7B:
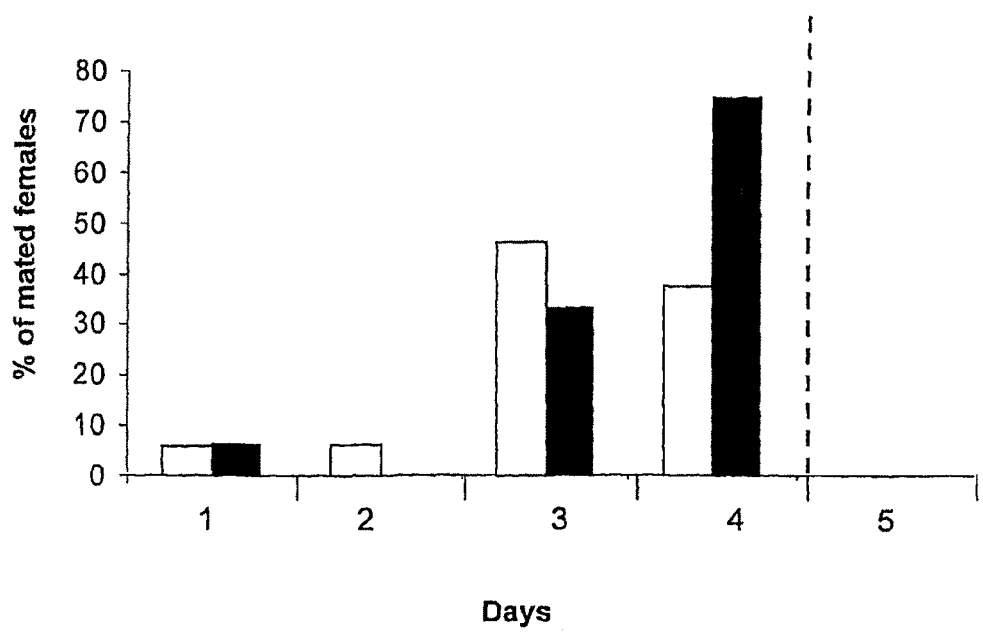
Figure 7C:
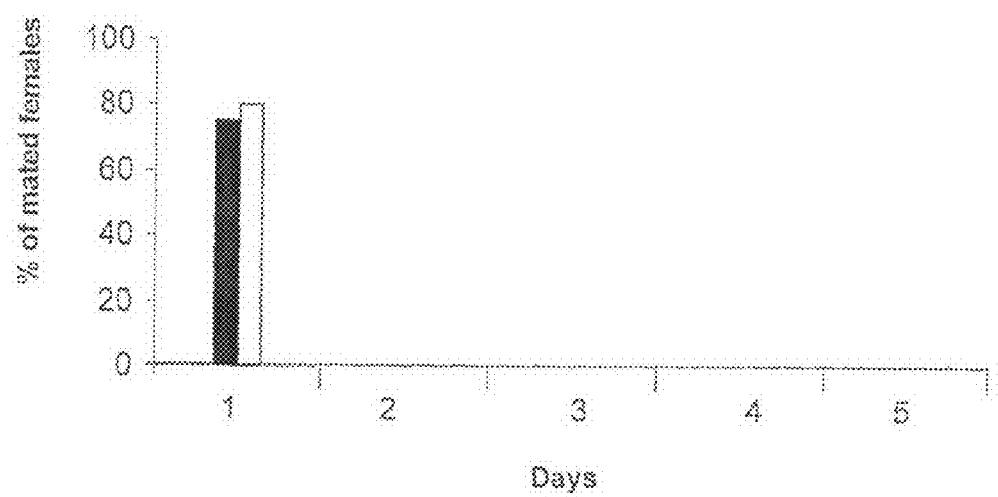
Figure 7D:
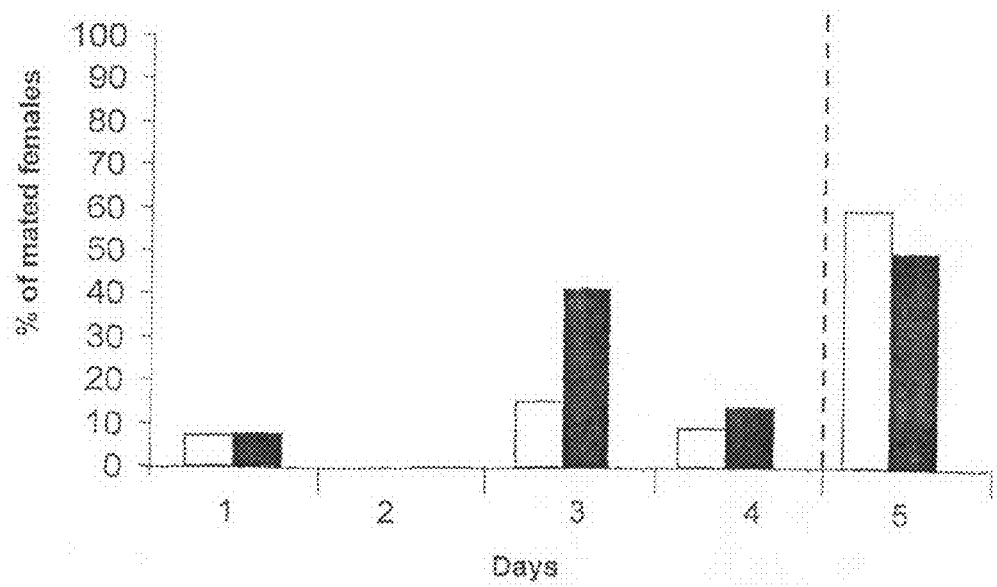

To examine the effect of the modified T-SP on female receptivity we first developed a sensitive bioassay that provided optimal conditions to test the transgenes. This experiment could have been preformed using wild type flies, but in order to ascertain that the transgene, even if it is not expressed, does not have unexpected effects on the flies' behavior, we used flies from the same genetic background as the transgenic T-SP flies (UAS-T-SP); i.e. transgenic females that carry a transgene but can not express it. We examined two independent lines to determine the effect of exposure to one or two males and whether a window of one hour would be sensitive enough to detect changes in female behavior. Four-day-old unmated females were placed with one or two males in a fresh food vial and their behavior was documented. Mated females were separated from males and left in the food vials. Twenty four hours later the females were re-exposed to unmated 3-day-old males and inspected for mating encounter and courting behavior for 1 hour. Females that did not mate after one hour and exhibited a rejection behavior were regarded as non-receptive female. We found that within one hour 80-90% of the females mated in the two lines examined (FIGS. 7A-B) and there was no difference if they were exposed to one or two males, suggesting that a length of one hour in enough to allow females to mate at high percentage. About 50% of the females re-mated after 4 to 5 days (FIGS. 7A-B). These results allowed us to set the threshold to evaluate the different transgenic lines. Females that exhibit non-receptivity above 4 days are, considered as females expressing a form of T-SP which is resistant to cleavage by hemolymph protease.

Since a change in the willingness of the female to mate is expressed in their behavior, we next developed a qualitative behavioral bioassay. Mated females reject the courting males by extruding their ovipositor toward the male and/or by kicking the courting male. Theses behaviors are not seen in unmated females. We set up a system in which we inspected whether or not the female kicks the male and extrudes her ovipositor toward the male (see material and methods), both of which are predictors of female receptivity status. We infer that if a transgene has an effect on a female it will be expressed in the number of female that will mate, when they will mate and if they exhibit rejection behavior.

Since heat-shock is used in some experiments to induce the transgenes, it was important to evaluate the effect of heat shock on female willingness to mate. Two lines that carry the transgenes but can not express the modified DrmSP$_{TSP}$ (FIG. 8A) and two lines of cy females that are the progeny of hsp70-GAL4; UAS-DrmSP$_{TSP}$ females but are not carrying or expressing the transgenes (FIG. 8B) were examined. The percentage of mating of females that were heat-shocked or not heat-shocked was compared and it was found that the exposure to heat had no effect on the transgenic female willingness to mate; 70-90% of the females that were exposed to the heat in both of the lines examined mated.

Example 7

T-SP is Expressed in Both Transgene Lines

Figure 9A:
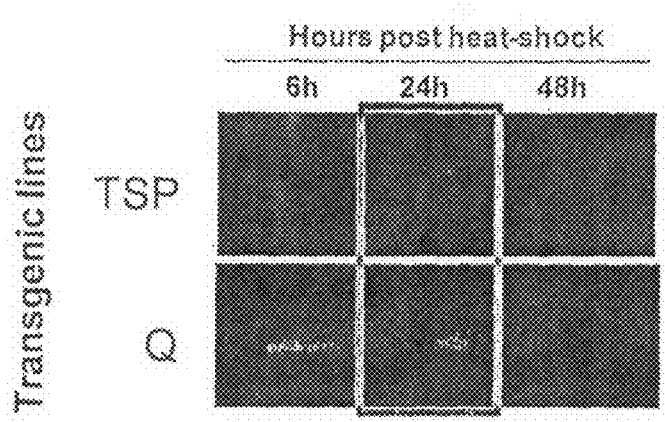
FIGS. 9A-B show T-SP transcript expression levels of (9A) transgenic females expressing unaltered T-SP, and Q mutation (T-$SP_Q$). The white box marks the first time post-heat-shock in which the modified T-SP is express.
Figure 9B:
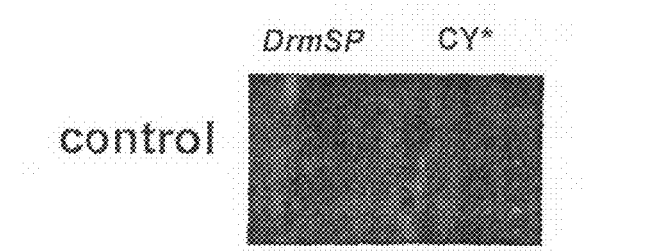

We next examined when the modified T-SP is first detected, when its expression is maximal and for how long we see such expression. We heat-shocked females that are expressing modified T-SP (hsp70-GAL4; UAS-T-SP$_X$), T-SP (hsp70-GAL4; UAS-T-SP) and their siblings (cy females) that are not expressing the different forms of T-SP, as negative control. After different lengths of time post heat-shock (6, 24 and 48 hrs) females were collected and mRNA was produced. Using specific primers for T-SP we examined by PCR the presence of a band at 100 bp. FIGS. 9A-B show that both lines expressed the modified T-SP and expression was first observed at 6 hrs post-mating. The expression levels of the different T-SP at the different times post-heat-shock were not significantly different. Since both lines expressed the modified T-SP at 24 hrs post-heat-shock, we examined the effect modified T-SP has on female receptivity at this time point.

Example 8

Ectopic Expression of T-SP in Unmated Female Induced Non-Receptivity

Figure 10:
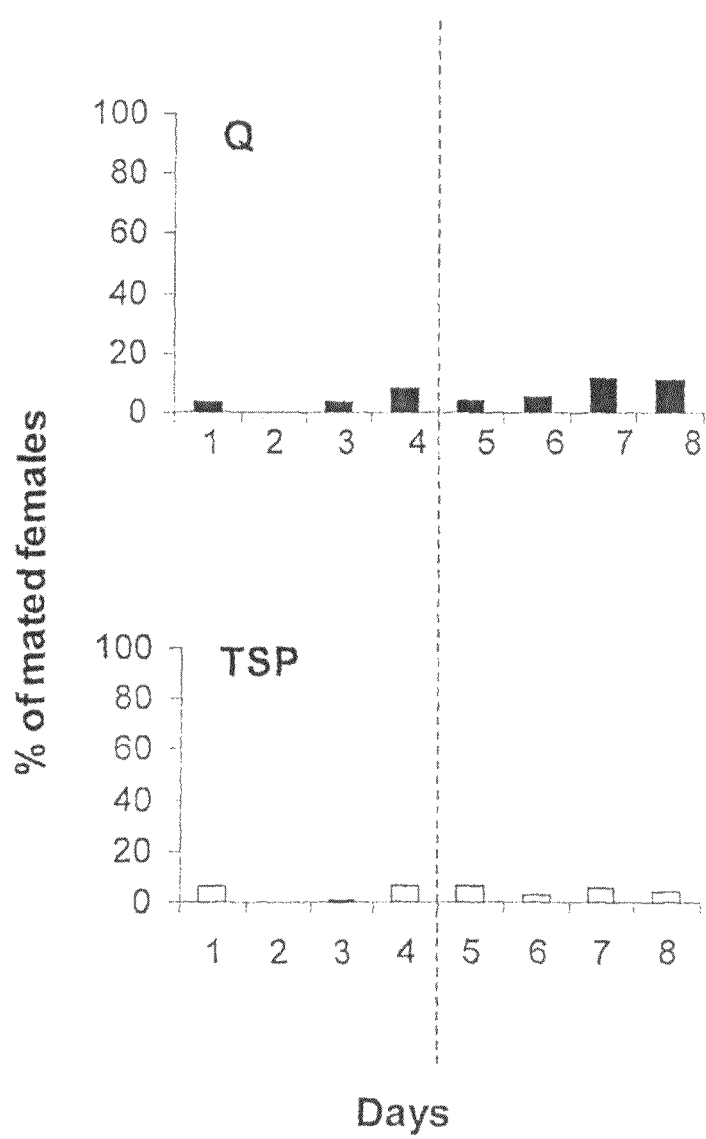
FIG. 10 shows that the modified T-$SP_Q$ and wild-type T-SP, expressed in unmated females by the heat-inducible GAL4 driver (hsp70-GAL4), induced female to be non-receptive for 8 days post-mating. The graph shows the percentage of females that re-mated at different days post-heat-shock. Q=T-$SP_Q$–two replicates, n=83; T-SP–two replicates, n=156. The dashed line represent the time that at least 50% of the females re-mated in the wild-type strain (4-5 days).

To examine the susceptibility to degradation of the different T-SP transgenes we first expressed the modified T-SP in unmated female by a heat-inducible GAL4 driver (hsp70-GAL4). We found that transgenes T-SP$_Q$ and T-SP, the latter being the wild-type form, had significant effect on female receptivity. Both lines showed lower percentage of mating during all 8 days of the experiment and passed the threshold lines (FIG. 10).

To verify that the induction of non-receptivity in these two specific lines is due to the biological activity of the peptide and not due to position effect, we examined another line for each of the transgenes. The results showed the same trend; T-SP$_Q$ and T-SP showed low re-mating rate (<10%) for all 8 days examined (FIG. 11). These results suggests that the there is no position effect.

Figure 12A:
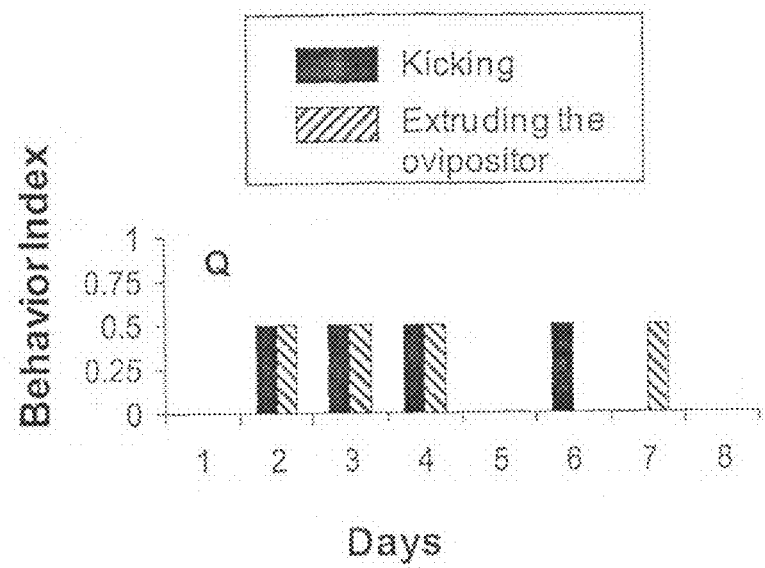
FIGS. 12A-B depicts behavior index of rejection behavior in T-$SP_Q$ (12A) and T-SP (12B) females towards courting males as a function of time post-mating. Black bars, kicking; hatched bars, extruding the ovipositor.
Figure 12B:
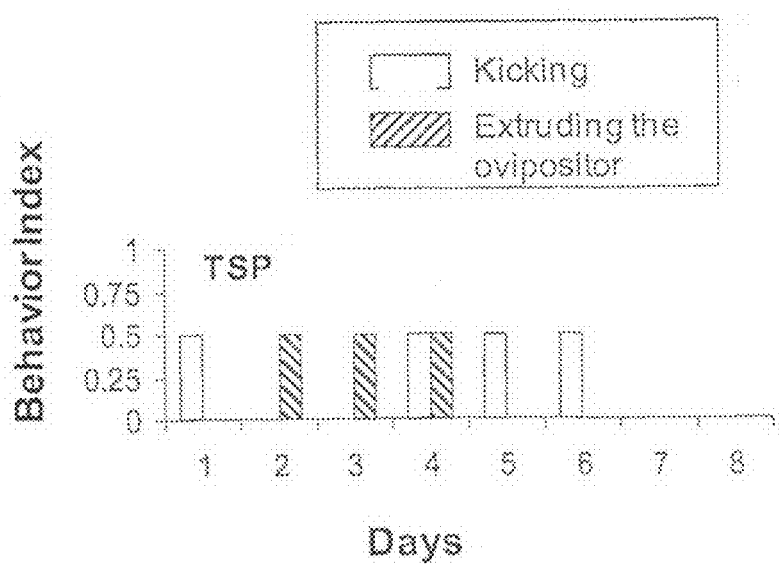

To further determine the effect of T-SP$_Q$ and T-SP on female receptivity we examined if the reduction in unmated female willingness to mate would also be accompanied by rejection behavior (see Material, Methods and Experimental Design). We found that in both lines the females exhibited rejection behavior (kicking and extruding her ovipositor) for all 8 days examined. We detected some differences in the pattern of behavior between flies carrying the two transgenes but this difference was not significant (FIGS. 12A-B). In both lines there was no significant difference between exposures to one or two males. In both lines a threshold could be drawn between 4-5 days. This threshold represent the time in which at least 50% of the wild-type females re-mated.

Taken together, our results show that ectopic expression of the modified form T-SP$_Q$ and the wild-type form T-SP induce non-receptivity in unmated females. One possible interpretation for the effect of the wild-type form is that the enzymes degrading DrmSP are not expressed in unmated females and thus there is no degradation. Perhaps T-SP is expressed for longer than 3 days and ongoing degradation is supplemented by the production of new molecules.

Figure 13:
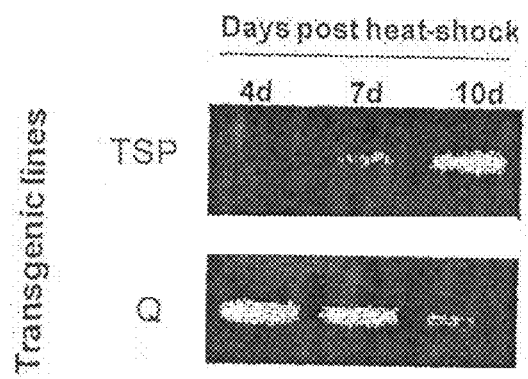
FIG. 13 shows that T-$SP_Q$ and T-SP are expressed in unmated females for at least 10 days post heat-shock.

To examine our hypothesis we next examined: (i) for how long T-SP$_Q$ and T-SP are expressed in unmated female and (ii) the effect of T-SP$_Q$ and T-SP when they are expressed in the male accessory glands and transmitted to the female in the male seminal fluid during mating. We found that indeed we can still see mRNA of T-SP$_Q$ and T-SP for at least 10 days post heat-shock (FIG. 13). This explains the high non-receptivity that females exhibited for 8 days post-heat-shock.

Females receiving the transgene T-SP commenced re-mating three days later, whereas those receiving the transgene T-SP$_Q$ commenced re-mating on day 5 after the first mating, and in lower percentages (FIG. 14). In addition, the behavior associated with imposed non-receptivity differed in the two cases: females receiving the T-SP$_Q$ transgene were more resolute in rejecting and repelling courting male during the non-receptive period (data not shown). Thus, expression of T-SP$_Q$ and T-SP in male accessory glands and their transfer to the female during normal mating indicates that indeed T-SP$_Q$ and not T-SP is responsible for the prolonged female receptivity.

In conclusion, we have now demonstrated "proof of concept": That the substitution of glutamine for arginine in a modified TSP$_Q$ transgene, specifically produced in the male reproductive accessory glands, significantly prolongs major features of female non-receptivity when transferred to the female during mating, as detailed herein. We attribute the sustained bioactivity of T-$SP_Q$ to its resistance to cleavage by trypsin, the major hemolymph endoprotease dominant in mated *D. melanogaster* females.

Example 9

Production of Transgenic Sterile *C. capitata* for Release into the Environment at Loci for Population Control 1. The Acp26Aa GAL4 driver line is amplified (transgenic insects carrying expression vector with GAL4 specifically expressed in the accessory glands).
2. The target line UAS-Drm$SP_Q$ is amplified (transgenic insects carrying expression vector with the UAS sequence controlling expression of the proteolysis-resistant sex peptide of SEQ ID NO: 11, which is not expressed in this line).
3. The driver line is cross-bred with the target line (the progeny express the mutated sex-peptide in the accessory glands of the male at the late pupal stage)
4. The pupae is thermally treated to kill the heat sensitive females.
5. The male pupae are harvested and irradiated for sterilization.
6. The pupae are transported to, and released at, loci for insect population control.

References

Backhaus, B., Sulkowski, E., Schlote, F. W., 1984. A semi-synthetic, general-purpose medium for *Drosophila melanogaster. D. I. S.* 60, 210-212.

Brand, A. H., Perrimon, N., 1993. Targeted gene expression as a means of altering cell fates and generating dominant phenotypes. *Development.* 118, 401-415.

Chapman, T., Bangham, J., Vinti, G., Seifried, B., Lung, O., Wolfner, M. F., Smith, H. K., Partridge, L., 2003. The sex peptide of *Drosophila melanogaster*: female post-mating responses analyzed by using RNA interference. *Proc Natl Acad Sci USA.* 100, 9923-9928.

Ding, Z., Haussmann, I., Ottiger, M., Kubli, E., 2003. Sex-peptides bind to two molecularly different targets in *Drosophila melanogaster* females. *J. Neurobiol.* 55, 372-384.

Domanitskaya, E. V., Liu, H., Chen, S., Kubli, E., 2007. The hydroxyproline motif of male sex peptide elicits the innate immune response in *Drosophila* females *FEBS J.* 274, 5659-5668.

Fan, Y., Rafaeli, A., Gileadi, C., Kubli, E., Applebaum, S. W. 1999. *Drosophila melanogaster* sex peptide stimulates juvenile hormone synthesis and depresses sex pheromone production in *Helicoverpa armigera. J. Insect Physiol.* 45, 127-133

Fan, Y., Rafaeli, A., Moshitzky, P., Kubli, E., Choffat, Y., Applebaum, S. W. 2000. Common functional elements of *Drosophila melanogaster* seminal peptides involved in reproduction of *Drosophila melanogaster* and *Helicoverpa armigera females. Insect Biochem. Mol. Biol.* 30, 805-812.

Klemenz, R., Weber, U., Gehring, W. I., 1987. The white gene as a marker in a new P-element vector for gene transfer in *Drosophila. Nucleic Acids Res.* 15, 3947-3959.

Lung, O., Wolfner, M. F., 1999. *Drosophila* seminal fluid proteins enter the circulatory system of the mated female fly by crossing the posterior vaginal wall. *Insect Biochem. Mol. Biol.* 29, 1043-1052.

McGuire, S E, Z. Mao, R. L. Davis, 2004. Spatiotemporal gene expression targeting with the TARGET and Gene-Switch systems in *Drosophila*. Sci. STKE 2004, p14.

Monsma, S. A., Wolfner, M. F., 1988. Structure and expression of a *Drosophila* male accessory gland gene whose product resembles a peptide pheromone precursor. *Genes Dev.* 2, 1063-1073.

Moshitzky, P., Fleischmann, I., Saudan, P., Klauser, S., Kubli, E., Applebaum, S. W., 1996. Sex-peptide activates juvenile hormone biosynthesis in *Drosophila melanogaster* corpus allatum. *Arch. Insect Biochem. Physiol.* 32, 363-374.

Moshitzky, P., Gilbert, L. I., Applebaum S. W. 2003. Biosynthetic maturation of the corpus allatum of the female adult medfly, *Ceratitis capitata*, and its putative control. *J. Insect Physiol.* 49, 603-609.

Park, M., Monsma, S. A. & Wolfner, M. F., 1994. Two tightly-linked *Drosophila* male accessory gland transcripts with the same developmental expression derive from independent transcription units. Mech. Dev. 48, 51-57.

Peng, J., Zipperlen, P., Kubli, E., 2005. *Drosophila* sex-peptide stimulates female innate immune system after mating via the Toll and Imd pathways. *Curr. Biol.* 15, 1690-1694.

Pilpel, N., Nezer, I., Applebaum, S. W., Heifetz, Y., 2008. Mating increases trypsin in female *Drosophila* hemolymph. *Insect Biochem. Mol. Biol.* 38, 320-330.

Schmidt, T., Choffat, Y., Klauser, S., Kubli, E. 1993. The *Drosophila melanogaster* sex-peptide: a molecular analysis of structure-function relationships. *J. Insect Physiol.* 39, 361-368.

Soller, M., Bownes, M., Kubli, E. 1997. Mating and sex peptide stimulate the accumulation of yolk in oocytes of *Drosophila melanogaster. Eur. J. Biochem.* 243, 732-738.

Styger, D. 1992. Molekulare Analyse des Sex peptidgens aus *Drosophila melanogaster*. Dissertation., Universität Zürich, Zürich.

Wolfner, M. F. 2007. "S.P.E.R.M." (seminal proteins (are) essential reproductive modulators): the view from *Drosophila. Soc. Reprod. Feral. Suppl.* 65, 183-199.

Wolfner, M. F., Heifetz, Y., Applebaum, S. W. (2005). Gonadal glands and their gene products. In: Comprehensive Molecular Insect Science (L. I. Gilbert, ed. in-chief; K. Iatrou and S. S. Gill, eds.) Vol 1: Reproduction and Development, 179-212.

The invention claimed is:

1. An isolated nucleic acid molecule comprising a polynucleotide sequence encoding an oligopeptide capable of prolonging post-mating depression of receptivity to mating in female insects as compared with wild type DrmSP, wherein said oligopeptide:
   (i) is derived from the Drosophila melanogaster sex peptide ("DrmSP") of the amino acid sequence as set forth in SEQ ID NO: 1, said oligopeptide consisting of the N-terminal signal peptide of DrmSP of the amino acid sequence as set forth in SEQ ID NO: 4, the N-terminal motif of DrmSP of the amino acid sequence as set forth in SEQ ID NO: 5 and the C-terminus of DrmSP of the amino acid sequence as set forth in SEQ ID NO: 3, or
   (ii) is derived from an active fragment of DrmSP comprising the N-terminal signal peptide of DrmSP of the amino acid sequence as set forth in SEQ ID NO: 4, and the C-terminus of DrmSP of the amino acid sequence as set forth in SEQ ID NO: 3, said oligopeptide (i) or active fragment (ii) being made resistant to proteolytic degradation by trypsin at a scissile bond within the C-terminus by neutral or conservative substitution of arginine 25 and/or lysine 26.

2. The isolated nucleic acid molecule according to claim 1, wherein said residue and/or said lysine residue of the trypsin cleavage site is substituted with a glutamine residue.

3. The isolated nucleic acid molecule according to claim 2, wherein said polynucleotide sequence encodes an oligopeptide derived from the oligopeptide as set forth in SEQ ID NO: 7, said oligopeptide comprising the N-terminal signal peptide of DrmSP of the amino acid sequence as set forth in SEQ ID NO: 4 linked to an amino acid sequence derived from the C-terminal amino acid sequence of DrmSP as set forth in SEQ ID NO: 3.

4. The isolated nucleic acid molecule according to claim 2, wherein said polynucleotide sequence is the polynucleotide sequence as set forth in SEQ ID NO: 9 encoding the oligopeptide comprising the amino acid sequence set forth in SEQ ID NO: 8, wherein Arg25 of SEQ ID NO: 3 has been substituted with glutamine.

5. The isolated nucleic acid molecule according to claim 2, wherein said polynucleotide sequence is the polynucleotide sequence as set forth in SEQ ID NO: 10 encoding the oligopeptide comprising the amino acid sequence set forth in SEQ ID NO: 11, wherein Arg25 of SEQ ID NO: 3 has been substituted with glutamine.

6. The isolated nucleic acid molecule according to claim 1, wherein said female insect is a member of an order selected from the group consisting of Anoplura, Hemiptera, Holometabola, Coleoptera, Diptera, Hymenoptera, Lepidoptera, Mecoptera, Megaloptera, Neuroptera, Siphonaptera, Strepsiptera, Trichoptera, Mallophaga, Psocoptera, Thysanoptera, Orthoptera, Blattaria, Dermaptera, Embioptera, Grylloblattodea, Isoptera, Mantodea, Mantophasmatodea, Plecoptera and Zoraptera.

7. The isolated nucleic acid molecule according to claim 6, wherein said insect is a member of the Diptera order.

8. An expression vector comprising a nucleic acid molecule comprising a polynucleotide sequence encoding an oligopeptide capable of prolonging post-mating depression of receptivity to mating in female insects as compared with wild type DrmSP, wherein said oligopeptide:
  (i) is derived from the Drosophila melanogaster sex peptide ("DrmSP") of the amino acid sequence as set forth in SEQ ID NO: 1, said oligopeptide consisting of the N-terminal signal peptide of DrmSP of the amino acid sequence as set forth in SEQ ID NO: 4, the N-terminal motif of DrmSP of the amino acid sequence as set forth in SEQ ID NO: 5 and the C-terminus of DrmSP of the amino acid sequence as set forth in SEQ ID NO: 3, or
  (ii) is derived from an active fragment of DrmSP comprising the N-terminal signal peptide of DrmSP of the amino acid sequence as set forth in SEQ ID NO: 4, and the C-terminus of DrmSP of the amino acid sequence as set forth in SEQ ID NO: 3,
said oligopeptide (i) or active fragment (ii) being made resistant to proteolytic degradation by trypsin at a scissile bond within the C-terminus by neutral or conservative substitution of arginine 25 and/or lysine 26.

9. The expression vector according to claim 8, wherein said nucleic acid molecule is operably linked to a promoter inducible by a non-endogenous transcription factor such as GAL4.

10. A transgenic insect comprising a nucleic acid molecule comprising a polynucleotide sequence encoding an oligopeptide capable of prolonging inducing post-mating depression of receptivity to mating in female insects as compared with wild type DrmSP, wherein said oligopeptide:
  (i) is derived from the Drosophila melanogaster sex peptide ("DrmSP") of the amino acid sequence as set forth in SEQ ID NO: 1, said oligopeptide consisting of the N-terminal signal peptide of DrmSP of the amino acid sequence as set forth in SEQ ID NO: 4, the N-terminal motif of DrmSP of the amino acid sequence as set forth in SEQ ID NO: 5 and the C-terminus of DrmSP of the amino acid sequence as set forth in SEQ ID NO: 3, or
  (ii) is derived from an active fragment of DrmSP comprising the N-terminal signal peptide of DrmSP of the amino acid sequence as set forth in SEQ ID NO: 4, and the C-terminus of DrmSP of the amino acid sequence as set forth in SEQ ID NO: 3,
said oligopeptide (i) or active fragment (ii) being made resistant to proteolytic degradation by trypsin at a scissile bond within the C-terminus by neutral or conservative substitution of arginine 25 and/or lysine 26.

11. The transgenic insect according to claim 10, wherein said nucleic acid molecule is operably linked to a promoter inducible by a non-endogenous transcription factor such as GAL4, and said transgenic insect further comprises a polynucleotide encoding the non-endogenous transcription factor operably linked to an accessory gland specific promoter such as 26Aa.

12. The transgenic insect according to claim 10, wherein said insect is at the developmental stage of fertilized egg, larval stage or pupal stage or said insect is a mature adult.

13. The transgenic insect according to claim 10, which is sexually sterile.

14. The transgenic insect according to claim 10, wherein said nucleic acid comprises a polynucleotide sequence as set forth in SEQ ID NO: 9 encoding the oligopeptide comprising the amino acid sequence set forth in SEQ ID NO: 8, wherein Arg25 of SEQ ID NO: 3 has been substituted with glutamine.

15. The transgenic insect according to claim 10, wherein said nucleic acid comprises a polynucleotide sequence as set forth in SEQ ID NO: 10 encoding the oligopeptide comprising the amino acid sequence set forth in SEQ ID NO: 11, wherein Arg25 of SEQ ID NO: 3 has been substituted with glutamine.

16. A method for biological control of a population of insects in a natural environment comprising releasing male transgenic insects into the environment at a locus for insect population control, wherein said transgenic insect comprises a nucleic acid molecule comprising a polynucleotide sequence encoding an oligopeptide capable of prolonging post-mating depression of receptivity to mating in female insects as compared with wild type DrmSP, wherein said oligopeptide:
  (i) is derived from the Drosophila melanogaster sex peptide ("DrmSP") of the amino acid sequence as set forth in SEQ ID NO: 1, said oligopeptide consisting of the N-terminal signal peptide of DrmSP of the amino acid sequence as set forth in SEQ ID NO: 4, the N-terminal motif of DrmSP of the amino acid sequence as set forth in SEQ ID NO: 5 and the C-terminus of DrmSP of the amino acid sequence as set forth in SEQ ID NO: 3, or
  (ii) is derived from an active fragment of DrmSP comprising the N-terminal signal peptide of DrmSP of the amino acid sequence as set forth in SEQ ID NO: 4, and the C-terminus of DrmSP of the amino acid sequence as set forth in SEQ ID NO: 3,
said oligopeptide (i) or active fragment (ii) being made resistant to proteolytic degradation by trypsin at a scissile bond within the C-terminus by neutral or conservative substitution of arginine 25 and/or lysine 26.

* * * * *

UNITED STATES PATENT AND TRADEMARK OFFICE
CERTIFICATE OF CORRECTION

PATENT NO.        : 8,677,934 B2
APPLICATION NO.   : 12/671620
DATED             : March 25, 2014
INVENTOR(S)       : Applebaum et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 899 days.

Signed and Sealed this

Twenty-ninth Day of September, 2015

Michelle K. Lee
*Director of the United States Patent and Trademark Office*

SEQUENCE LISTING

<160> NUMBER OF SEQ ID NOS: 12

<210> SEQ ID NO 1
<211> LENGTH: 55
<212> TYPE: PRT
<213> ORGANISM: Drosophila melanogaster

<400> SEQUENCE: 1

Met Lys Thr Leu Ala Leu Phe Leu Val Leu Val Cys Val Leu Gly Leu
1               5                   10                  15

Val Gln Ser Trp Glu Trp Pro Trp Asn Arg Lys Pro Thr Lys Phe Pro
            20                  25                  30

Ile Pro Ser Pro Asn Pro Arg Asp Lys Trp Cys Arg Leu Asn Leu Gly
        35                  40                  45

Pro Ala Trp Gly Gly Arg Cys
    50                  55

<210> SEQ ID NO 2
<211> LENGTH: 36
<212> TYPE: PRT
<213> ORGANISM: Drosophila melanogaster

<400> SEQUENCE: 2

Trp Glu Trp Pro Trp Asn Arg Lys Pro Thr Lys Phe Pro Ile Pro Ser
1               5                   10                  15

Pro Asn Pro Arg Asp Lys Trp Cys Arg Leu Asn Leu Gly Pro Ala Trp
            20                  25                  30

Gly Gly Arg Cys
        35

<210> SEQ ID NO 3
<211> LENGTH: 29
<212> TYPE: PRT
<213> ORGANISM: Drosophila melanogaster

<400> SEQUENCE: 3

Lys Pro Thr Lys Phe Pro Ile Pro Ser Pro Asn Pro Arg Asp Lys Trp
1               5                   10                  15

Cys Arg Leu Asn Leu Gly Pro Ala Trp Gly Gly Arg Cys
            20                  25

<210> SEQ ID NO 4
<211> LENGTH: 19
<212> TYPE: PRT
<213> ORGANISM: Drosophila melanogaster

<400> SEQUENCE: 4

Met Lys Thr Leu Ala Leu Phe Leu Val Leu Val Cys Val Leu Gly Leu
1               5                   10                  15

Val Gln Ser

<210> SEQ ID NO 5
<211> LENGTH: 7
<212> TYPE: PRT
<213> ORGANISM: Drosophila melanogaster

<400> SEQUENCE: 5

Trp Glu Trp Pro Trp Asn Arg
1               5

```
<210> SEQ ID NO 6
<211> LENGTH: 165
<212> TYPE: DNA
<213> ORGANISM: Drosophila melanogaster

<400> SEQUENCE: 6
atgaaaactc tagctctatt cttggttctc gtttgcgtac tcggcttggt ccagtcctgg      60
gaatggccgt ggaataggaa gcctacaaag tttccaattc caagcccaa tcctcgtgat     120 aagtggtgcc gtcttaattt ggggcccgcc tggggtggaa gatgt                    165

<210> SEQ ID NO 7
<211> LENGTH: 48
<212> TYPE: PRT
<213> ORGANISM: Artificial Sequence
<220> FEATURE:
<223> OTHER INFORMATION: SYNTHETIC

<400> SEQUENCE: 7

Met Lys Thr Leu Ala Leu Phe Leu Val Leu Val Cys Val Leu Gly Leu
1               5                   10                  15

Val Gln Ser Lys Pro Thr Lys Phe Pro Ile Pro Ser Pro Asn Pro Arg
            20                  25                  30

Asp Lys Trp Cys Arg Leu Asn Leu Gly Pro Ala Trp Gly Gly Arg Cys
        35                  40                  45

<210> SEQ ID NO 8
<211> LENGTH: 48
<212> TYPE: PRT
<213> ORGANISM: Artificial Sequence
<220> FEATURE:
<223> OTHER INFORMATION: SYNTHETIC

<400> SEQUENCE: 8

Met Lys Thr Leu Ala Leu Phe Leu Val Leu Val Cys Val Leu Gly Leu
1               5                   10                  15

Val Gln Ser Lys Pro Thr Lys Phe Pro Ile Pro Ser Pro Asn Pro Arg
            20                  25                  30

Asp Lys Trp Cys Gln Leu Asn Leu Gly Pro Ala Trp Gly Gly Arg Cys
        35                  40                  45

<210> SEQ ID NO 9
<211> LENGTH: 144
<212> TYPE: DNA
<213> ORGANISM: Artificial Sequence
<220> FEATURE:
<223> OTHER INFORMATION: SYNTHETIC

<400> SEQUENCE: 9
atgaaaactc tagctctatt cttggttctc gtttgcgtac tcggcttggt ccagtccaag      60
cctacaaagt ttccaattcc aagccccaat cctcgtgata agtggtgcca gcttaatttg     120
gggcccgcct ggggtggaag atgt                                             144

<210> SEQ ID NO 10
<211> LENGTH: 165
<212> TYPE: DNA
<213> ORGANISM: Artificial Sequence
<220> FEATURE:
<223> OTHER INFORMATION: SYNTHETIC

<400> SEQUENCE: 10
atgaaaactc tagctctatt cttggttctc gtttgcgtac tcggcttggt ccagtcctgg      60
gaatggccgt ggaataggaa gcctacaaag tttccaattc caagccccaa tcctcgtgat     120
```

```
aagtggtgcc agcttaattt ggggcccgcc tgggtggaa gatgt                    165
```

<210> SEQ ID NO 11
<211> LENGTH: 55
<212> TYPE: PRT
<213> ORGANISM: Artificial Sequence
<220> FEATURE:
<223> OTHER INFORMATION: SYNTHETIC

<400> SEQUENCE: 11

```
Met Lys Thr Leu Ala Leu Phe Leu Val Leu Val Cys Val Leu Gly Leu
1               5                   10                  15

Val Gln Ser Trp Glu Trp Pro Trp Asn Arg Lys Pro Thr Lys Phe Pro
            20                  25                  30

Ile Pro Ser Pro Asn Pro Arg Asp Lys Trp Cys Gln Leu Asn Leu Gly
        35                  40                  45

Pro Ala Trp Gly Gly Arg Cys
    50                  55
```

<210> SEQ ID NO 12
<211> LENGTH: 29
<212> TYPE: PRT
<213> ORGANISM: Artificial Sequence
<220> FEATURE:
<223> OTHER INFORMATION: SYNTHETIC

<400> SEQUENCE: 12

```
Lys Pro Thr Lys Phe Pro Ile Pro Ser Pro Asn Pro Arg Asp Lys Trp
1               5                   10                  15

Cys Gln Leu Asn Leu Gly Pro Ala Trp Gly Gly Arg Cys
            20                  25
```